US011020220B2

(12) United States Patent
Raquin et al.

(10) Patent No.: US 11,020,220 B2
(45) Date of Patent: Jun. 1, 2021

(54) CASSETTE FOR RECEIVING AN INTRAOCULAR LENS, INJECTOR DEVICE HAVING SAID CASSETTE AND METHOD FOR FOLDING AN INTRAOCULAR LENS IN A CASSETTE

(71) Applicant: Carl Zeiss Meditec AG, Jena (DE)

(72) Inventors: Vincent Raquin, La Rochelle (FR); Dmitry Pankin, Berlin (DE); Brian Rathert, Recklinghausen (DE)

(73) Assignee: Carl Zeiss Meditec AG, Jena (DE)

( * ) Notice: Subject to any disclaimer, the term of this patent is extended or adjusted under 35 U.S.C. 154(b) by 498 days.

(21) Appl. No.: 14/949,709

(22) Filed: Nov. 23, 2015

(65) Prior Publication Data

US 2016/0074156 A1 Mar. 17, 2016

Related U.S. Application Data

(63) Continuation of application No. PCT/EP2014/057289, filed on Apr. 10, 2014.

(30) Foreign Application Priority Data

May 21, 2013 (DE) .................... 10 2013 105 185.5

(51) Int. Cl.
*A61F 2/16* (2006.01)
*B65B 63/04* (2006.01)
(52) U.S. Cl.
CPC ............ *A61F 2/1678* (2013.01); *B65B 63/04* (2013.01)
(58) Field of Classification Search
CPC ................. A61F 2/1678; A61F 2/0095; A61F 2/1662–1678; A61F 2/1691;
(Continued)

(56) References Cited

U.S. PATENT DOCUMENTS 5,947,975 A * 9/1999 Kikuchi ................ A61F 2/1664
606/107
7,798,988 B2 * 9/2010 Aubert .............. A61M 37/0069
604/117

(Continued)

FOREIGN PATENT DOCUMENTS

| EP | 2161006 A1 | 3/2010 |
|---|---|---|
| FR | 2 820 633 A1 | 8/2002 |
| JP | 2005087771 A | 4/2005 |

OTHER PUBLICATIONS

English translation of International Preliminary Report on Patentability of the international searching authority dated Nov. 24, 2015 in international patent application PCT/EP2014/057289 on which the claim of priority is based.

(Continued)

*Primary Examiner* — Tan-Uyen T Ho
*Assistant Examiner* — Charles M Wei
(74) *Attorney, Agent, or Firm* — Walter Ottesen, P.A.

(57) ABSTRACT

The invention is directed to a cassette for accommodating an intraocular lens. The cassette defines a longitudinal axis and includes a base part. Pivotable cover flaps are arranged on the base part so as to be pivotable about the longitudinal axis from a base position to a closed position. The cover flaps are curved at least in selected regions thereof and are configured to be autonomously intrinsically bendable in a defined manner when the cover flaps are moved from the base position to the closed position.

28 Claims, 15 Drawing Sheets

(58) Field of Classification Search
CPC . A61B 5/6838; A61B 5/6884; A61B 17/0487; A61B 17/08; A61B 17/105; A61B 17/122; A61B 17/7047; A61B 2017/2808; A61M 37/0069
See application file for complete search history.

(56) References Cited

U.S. PATENT DOCUMENTS

| | | | |
|---|---|---|---|
| 8,454,625 B2 | 6/2013 | Yoshida et al. | |
| 8,470,031 B2 * | 6/2013 | Pankin | A61F 2/1678 623/6.12 |
| 8,834,412 B2 * | 9/2014 | Painchaud | A61M 37/0069 604/198 |
| 2004/0267359 A1 | 12/2004 | Makker et al. | |
| 2005/0065534 A1 * | 3/2005 | Hohl | A61F 2/1678 606/107 |
| 2011/0046634 A1 * | 2/2011 | Rathert | A61F 2/1664 606/107 |

OTHER PUBLICATIONS

International Search Report dated Jun. 23, 2014 of international application PCT/EP2014/057289 on which this application is based.
Office action of the Indian Intellectual Property Office dated Mar. 17, 2020 in corresponding Indian patent application 10586/DELNP/2015.

* cited by examiner

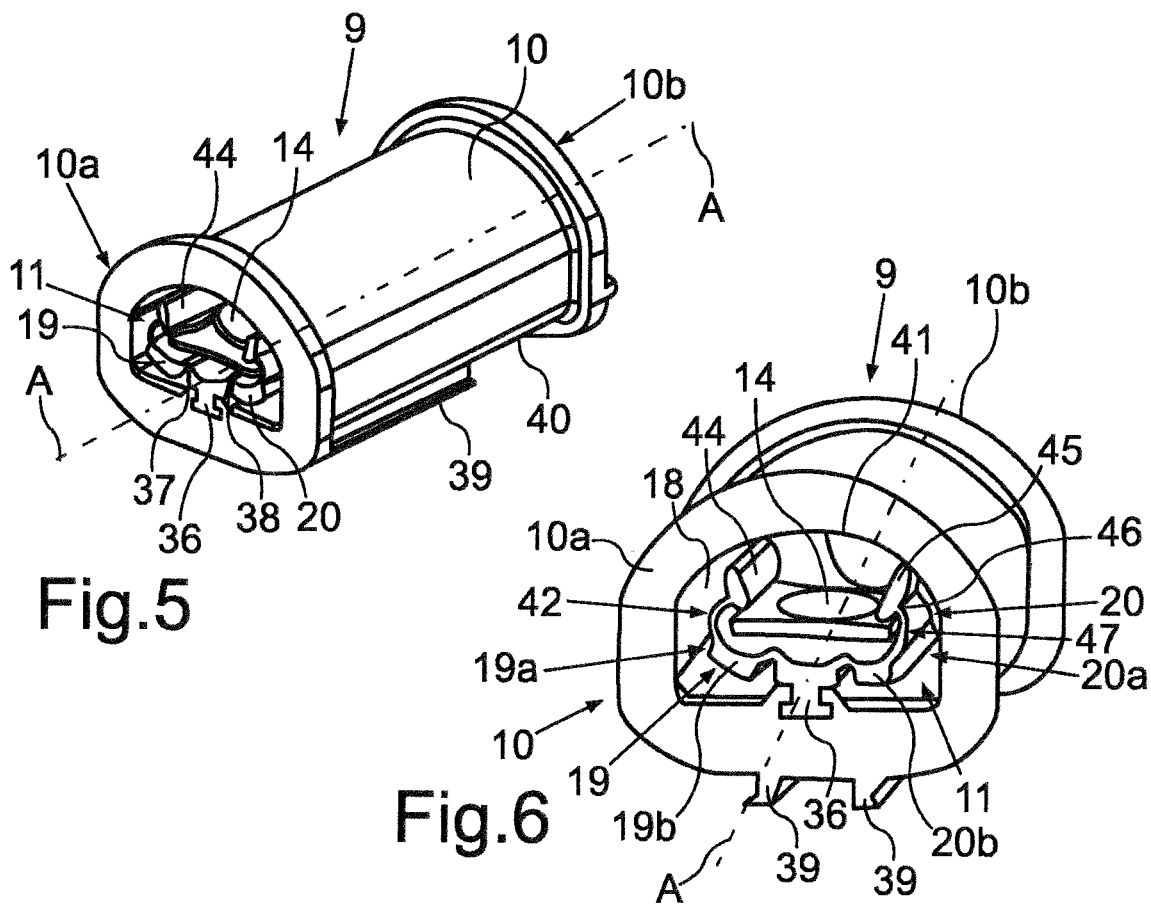
Fig.5
Fig.6
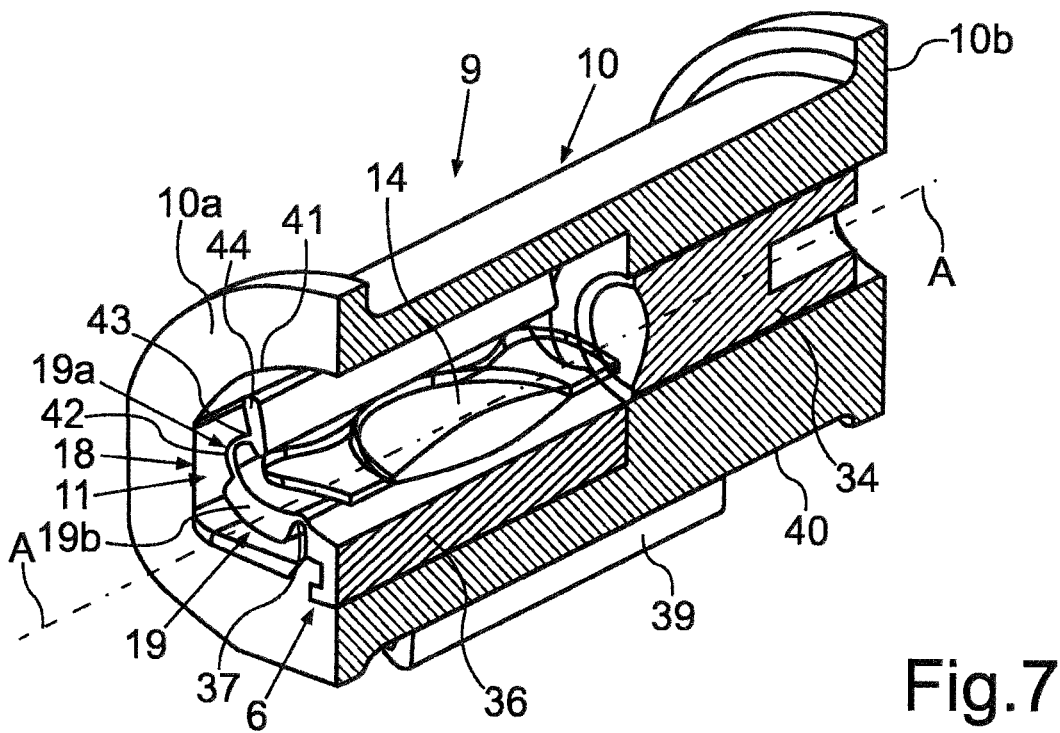
Fig.7

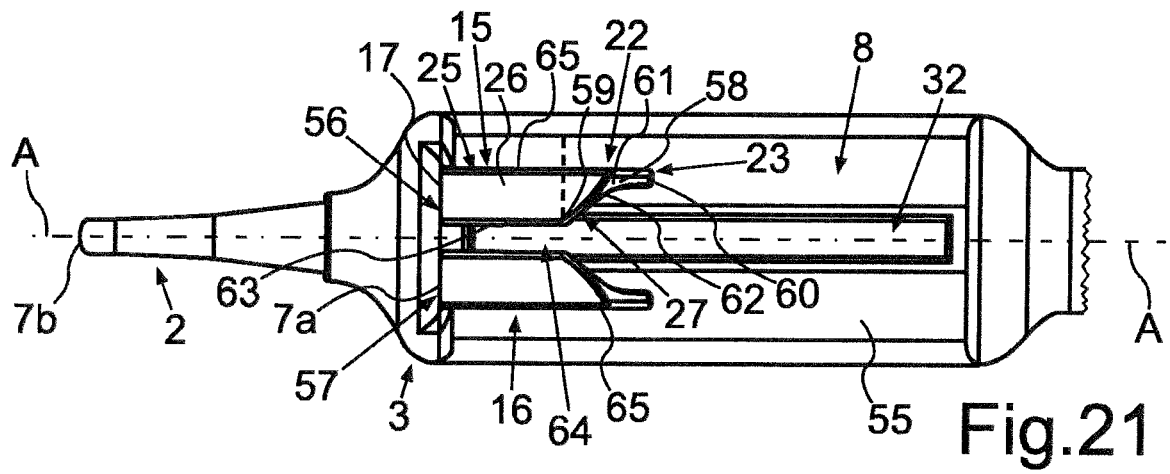
Fig.21
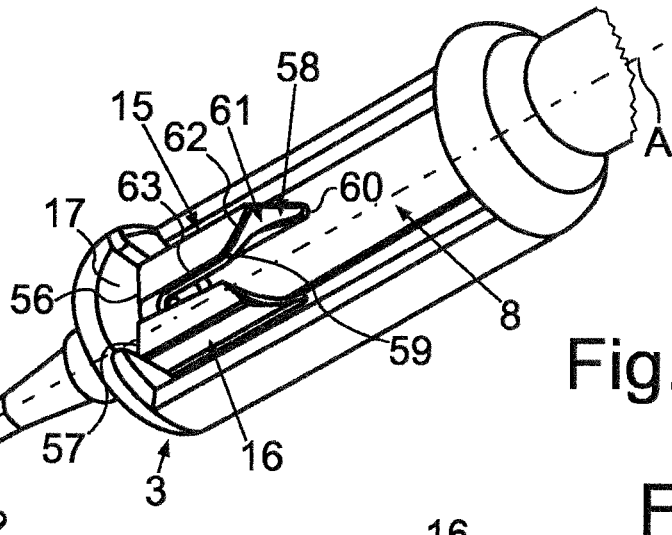
Fig.22
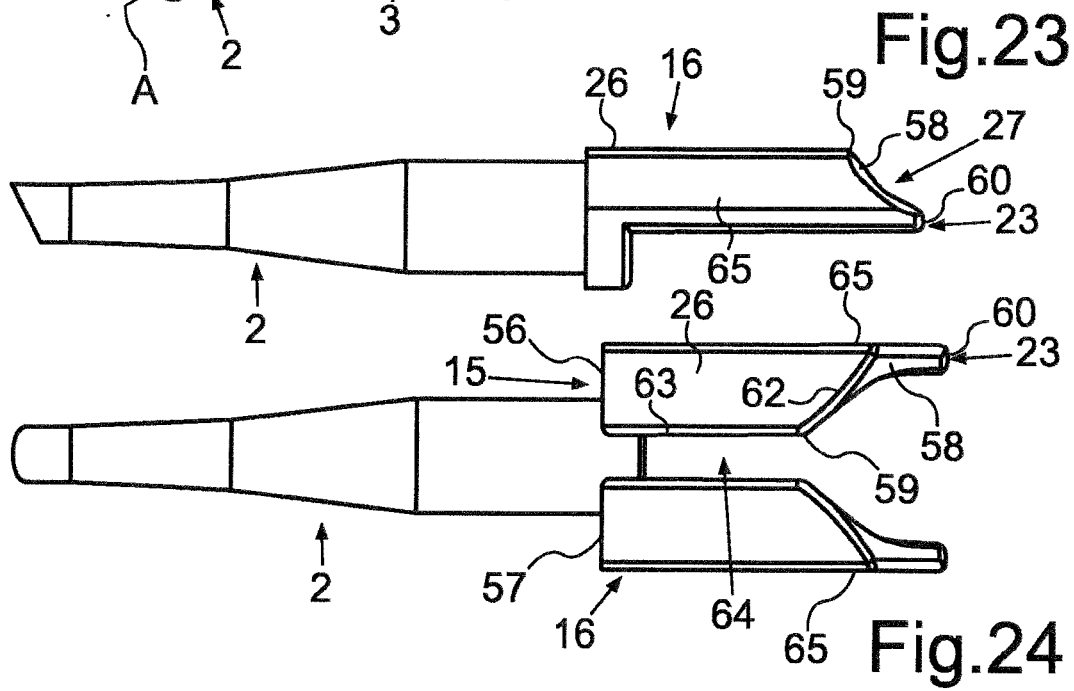
Fig.23
Fig.24

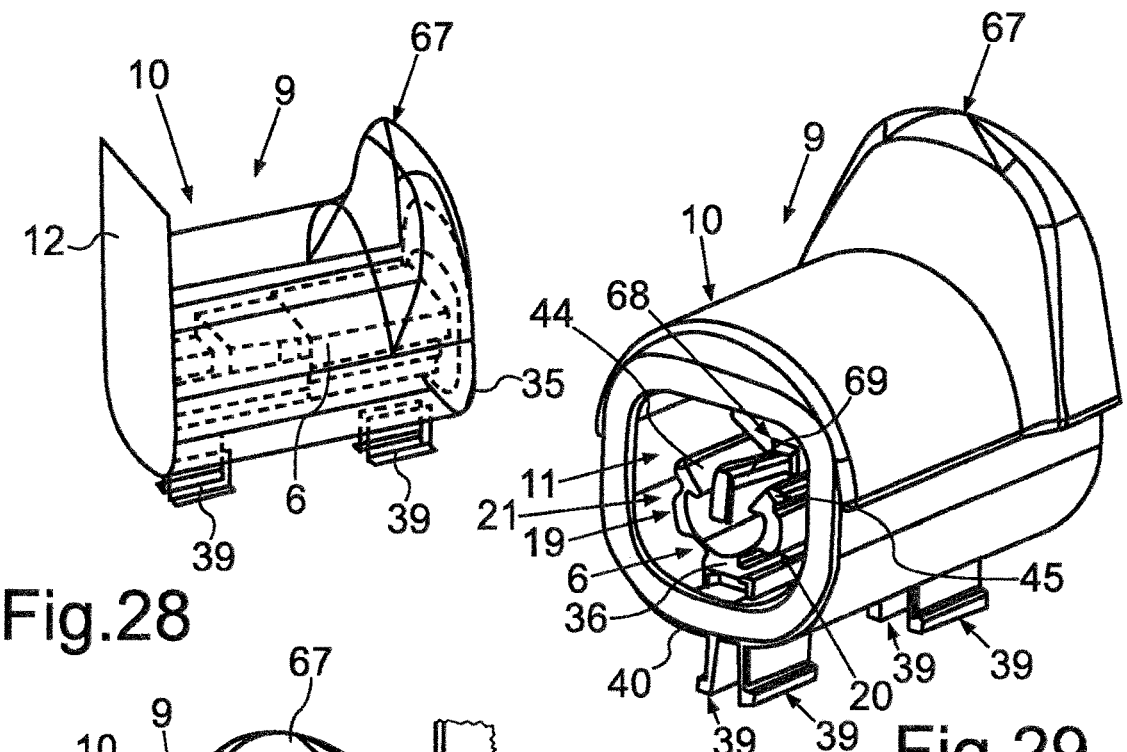
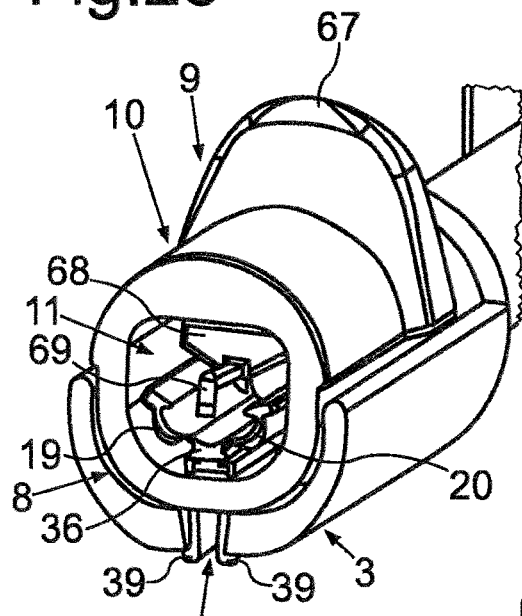
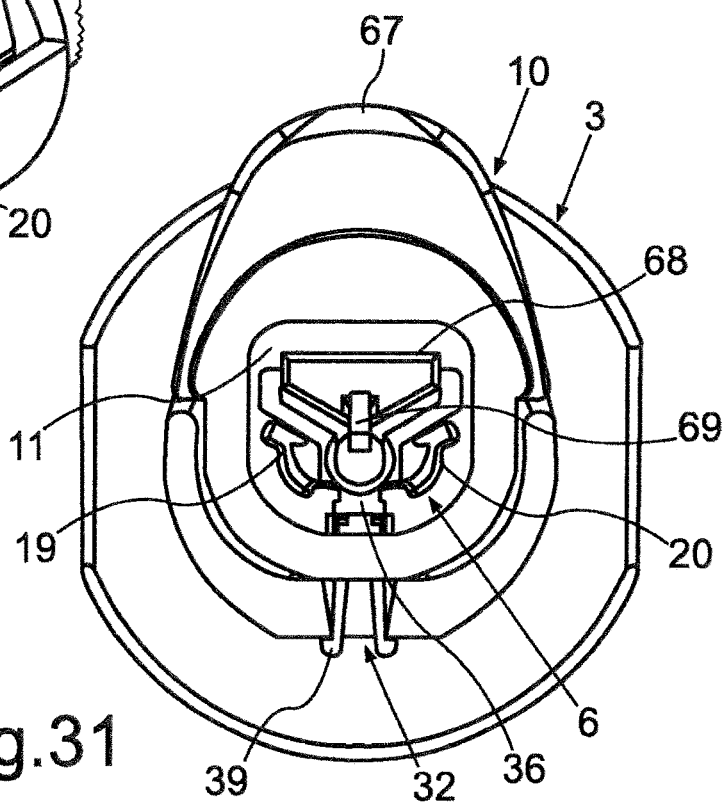

CASSETTE FOR RECEIVING AN INTRAOCULAR LENS, INJECTOR DEVICE HAVING SAID CASSETTE AND METHOD FOR FOLDING AN INTRAOCULAR LENS IN A CASSETTE

CROSS REFERENCE TO RELATED APPLICATIONS

This application is a continuation application of international patent application PCT/EP2014/057289, filed Apr. 10, 2014, designating the United States and claiming priority from German application 10 2013 105 185.5, filed May 21, 2013, and the entire content of both applications is incorporated herein by reference.

FIELD OF THE INVENTION

The invention relates to a cassette for receiving an intraocular lens. The cassette includes a base part, on which cover flaps pivotable around the longitudinal axis of the cassette relative to the base part are disposed. The invention also relates to an injector device for introducing an intraocular lens into an eye, which has a cassette. The invention also relates to a method for folding an intraocular lens in an injector device for introducing an intraocular lens into an eye.

BACKGROUND OF THE INVENTION

Intraocular lenses are inserted into an eye as implants and replace the natural lens. Thereto, injector devices are provided, which have a piston guided in an injector tube. A receiving space for the intraocular lens is formed at the front end of the injector tube, wherein this receiving space can be formed in a separate cassette, which can be introduced into a frame of the injector tube. It can also be provided that the receiving space is formed integrally in the injector tube. Moreover, an injector tip is formed towards the front adjoining to the receiving space, which has a guide channel, in which the intraocular lens is pushed through after shifting out of the receiving space and exits at the front in a folded state and is inserted into the eye. The front side of the tip is directly introduced into the eye.

In known intraocular lenses, with conventional known injector tips and injector devices, the problem occurs that they either roll together in uncoordinated manner with regard to folding thereof such that especially with asymmetric lenses, which have an optical part with different curved surfaces, the folding is optionally effected in an undesired direction.

From United States patent application publication 2004/0267359 A1, an injector tip for an injector device is known, which has a cassette rearward adjoining to a rear inlet in integrated manner, in which the intraocular lens can be stored. The cassette includes two cover flaps, which are pivotable relatively to each other around a longitudinal axis of the injector tip. The cassette includes two groove-like receptacles, wherein each one groove-like receptacle is associated with a cover. The intraocular lens is disposed in these groove-like receptacles, wherein a tubular receptacle forms of the groove-like receptacles upon closing the covers, in which the lens is pre-folded, before it can enter the injector tip. Plate-like elements are formed to the respective groove-like receptacles, which abut on each other with the contact surfaces in the closed state of the covers.

Moreover, from U.S. Pat. No. 5,947,975, a cassette for an intraocular lens is known, in which a base body is formed, to which intrinsically rigid cover flaps are formed on the opposing sides, which are disposed thereon pivotable relative to the base part. The lens is disposed in bearing pedestals of these cover flaps and it is deformed in closing the cover flaps.

In the known implementations, the pre-folding of the lens before entry thereof into the injector tip is restricted due to the configuration of the cassette with regard to the procedure in folding.

SUMMARY OF THE INVENTION

It is an object of the invention to provide a cassette for receiving an intraocular lens, an injector device having a cassette as well as a method for folding an intraocular lens in a cassette.

A cassette according to the invention is formed for receiving an intraocular lens, wherein the cassette is formed for assembly to an injector device for introducing the intraocular lens into an eye. The cassette comprises a base part, on which two cover flaps are disposed movable relative thereto, especially pivotable. The two cover flaps are especially intrinsically deformable in non-destructive manner. This means that they are bendable in defined manner starting from a base shape perpendicular to the longitudinal axis of the cassette without destruction such that the bent shape of a cover flap can be changed in this context. This flexible intrinsic deformation of the cover flaps is therefore possible to the effect that the fundamental base shape of a cover flap can be changed with a bent shape preferably at least in sections and thus this bending can be decreased and increased. This intrinsic deformation of a cover flap can be reversibly feasible in non-destructive manner and thus repeatable multiple times. By such a configuration of intrinsically deformable cover flaps of the cassette, the folding of the intraocular lens in the cassette can be very individually and definedly influenced in closing the cover flaps, in particular with such a closing movement and thus with pivoting of the cover flaps about the longitudinal axis of the cassette. Therein, intrinsic deformation and thus bending of the cover flaps is in particular provided in such a pivoting movement of the cover flaps around the longitudinal axis such that the cover flaps are virtually bent towards the longitudinal axis viewed in a plane perpendicular to the longitudinal axis.

In particular in a base position of arc-shaped flap sections, the cover flaps are curved at least in certain areas and intrinsically bendable in a defined and autonomous manner by closing in the cover flaps.

In an advantageous implementation of this cassette, each cover flap has a hammerhead-shaped or T-shaped thickening at a free end facing away from the base part. By this configuration, the guided pivoting of the cover flaps is again favored in particular by closing tips of an injector device since especially when the pivoting movement is already far advanced and the position of the cover flaps is close to the final position, slipping through of the cover flaps besides the closing tips is not possible and thus undesired reopening of the cover flaps is prevented. Moreover, by such a configuration of the ends of the cover flaps, a mechanically very stable and self-retaining configuration is also achieved such that in particular also in the closed state of the cover flaps, a mechanically self-stabilizing structure closed in the cross-section is provided. This is particularly advantageous especially in the intrinsically bendable cover flaps, which are then retained in the closed state by these more robust and mechanically stable hammerhead-shaped or T-shaped thickenings and thus no collapse of the cover flaps at all occurs, but the very symmetric cross-sectional shape of the closed cassette is maintained.

Preferably, it is provided that the hammerhead-shaped thickenings are shaped such that they at least temporarily seat on the intraocular lens as folding stabilizers upon pivoting the cover flaps into the closed position. Thereby, the lens is virtually encompassed to a certain extent in particular in its lateral areas, in particular in the optical part, and the folding scenario is supported and promoted.

Preferably, the cover flaps are formed such that upon closing the cover flaps, first, only outer ends of the thickenings are contacted, and the flap sections are deformable by further closing and abutting on each other of the thickenings. Thereby, a particularly precise and self-triggering mechanism is formed, which specifically guides the deformation of the flap sections, and thereby the desired folding of the lens in the cassette is performed.

Thus, upward slipping away of the intraocular lens in pre-folding in the cassette is preferably also prevented.

Preferably, it is provided that each thickening has an end-side contact surface, the radial dimensions of which are larger than a radial thickness of the cover flap outside of the hammerhead-shaped or hammerhead-like thickening.

Preferably, it is provided that the cassette and the closing tips are disposed displaceable relative to each other viewed in axial direction. By such a configuration, the pre-folding of the lens in the cassette is feasible in much favored and defined manner.

Preferably, outer sides of the cover flaps do not have a stepless contour course viewed in cross-section, but are stepped. Preferably, at least one elevation is formed on an outer side. In particular, the elevation is formed for guiding engagement of closing tips for automatically closing the cover flaps.

Preferably, a flap section formed between an elevation and an end-side thickening viewed in cross-section (plane perpendicular to the longitudinal axis) and thinner compared thereto (radially considered) is non-destructively intrinsically bendable, in particular only the section or area is bendable. By this specific local position and/or length of the intrinsically bendable area in relation to other parts of a cover flap, particular advantages with respect to improved folding scenario of the lens in the cassette are achieved.

In particular, it is provided that a cover flap, in particular the flap section, is reversibly intrinsically deformable such that the deformation can be repeatedly caused and again returned.

However, it can also be provided that the intrinsic deformation is effected plastically in defined manner and thus only once.

In particular, the deformation is inducible if end pieces or outer ends of two cover flaps contact from closing the cover flaps, but the end pieces are not yet in the final position such that in the further closing operation, by the supporting forces of the end pieces to each other, the desired deformation of the cover flaps, in particular of the flap sections, automatically arises. This is then preferably effected without further mechanical support of the end pieces on other components.

An injector device according to the invention for introducing an intraocular lens into an eye includes a cassette according to the invention or an advantageous implementation thereof.

It in particular also includes an injector tip with a continuous guide channel for the intraocular lens. The guide channel has a rear inlet and a front outlet. This is seen in the direction of the longitudinal axis of the injector tip and thus also of the guide channel as well as therefore also of the injector device. Therein, the rear inlet denotes that location, on which an intraocular lens enters the injector tip to then be passed through and to again exit at the front outlet and then to be introduced into the eye.

The injector device includes at least two closing tips, which are formed for closing a cassette receiving the intraocular lens. The two closing tips extend axially further rearwards than the rear inlet viewed in the direction of the longitudinal axis of the injector device. With the configuration with respect to number and shape as well as the local position of the closing tips, folding of an intraocular lens in the injector device can be improved. The closing tips, which can also be referred to as prongs or blades, allow a very adequate beginning of the folding of the intraocular lens exact in position as well as exact in situation and time as well as the following folding such that undesired abrupt folding operations or undesired foldings in shape and position of the intraocular lens can be prevented.

Preferably, it is provided that the closing tips extend spaced and parallel to each other in the direction of the longitudinal axis of the injector device. By such an arrangement, with a relative movement between the closing tips and the cassette receiving the intraocular lens, which is performed in axial direction, particularly uniform pivoting of cover flaps of the cassette is allowed. Undesired abrupt folding operations of the intraocular lens, which optionally are associated with undesired force applications as well as force peaks, can thereby be prevented. In this context, thus, undesired slipping or twisting of the lens in the cassette can also be prevented. By the spaced arrangement of the closing tips, a further advantage with respect to the lever forces then to be generated on the cover flaps is also achieved, and with further axial displacement of the components to each other, thus, lateral support of the cover flaps by the closing tips is also virtually allowed. Thus, the cassette can virtually be laterally supported by the closing tips such that they are configured in multifunctional manner. Besides their function of closing the cover flaps of the cassette in this axial relative displacement, in addition, the guiding function and lateral stabilization of the cassette by these closing tips is added. Especially by the arrangement and the shape of the closing tips, the exact axial displacement of the cassette is also stabilized on the one hand.

Preferably, it is provided that the closing tips are formed and disposed symmetrically to each other to the longitudinal axis. The above mentioned advantages are thereby once again favored.

Preferably, it is provided that free rear ends of the closing tips are formed tapered and each have a bent guiding surface. Such a configuration is particularly advantageous since in contacting the closing tips with the cassette, a barrier then does not have to be overcome here too, which results in stopping of the axial displacement movement and furthermore then increased force effort for overcoming this barrier would be required. By this specific shaping of the closing tips, this can be prevented, and a jerk-free and continuous sequence of movement for axial displacement is also allowed in contacting the closing tips with the cassette and also thereafter. The jerk-free and uniform pivoting movement of the cover flaps is particularly favorably achieved by these bent guiding surfaces. Incidentally, here too, the already above mentioned advantages with respect to the desired folding of the intraocular lens in the cassette then particularly emerge.

Preferably, it is provided that in a preferred implementation the guiding surface has a steep turn-like rear section. This contorted section, which also virtually represents a short section of a helix winding, allows the above mentioned advantages with respect to a very uniform pivoting movement of the cover flaps of the cassette around the longitudinal axis of the injector device with also continuing axial relative displacement between the closing tips and the cassette.

Preferably, it is provided that this steep turn-like rear section begins with a rear end at the free end of a closing tip, which is further spaced in linear connection to the longitudinal axis of the injector device than a front end of this steep turn-like rear section. This means that the position of the steep turn-like rear section curves in the direction towards the longitudinal axis beginning from the rear end. Such a configuration again considerably confirms the above mentioned advantages. Moreover, in such a configuration, it is also achieved that the funnel-like guiding of the cover flaps of the cassette to be pivoted to a front section of the guiding surface is favored. This front section is then preferably formed as a slit, which serves for guiding the then already in particular closed cover flaps with further axial displacement of the cassette relative to the closing tips.

Preferably, it is provided that the inclination of the guiding surface at the rear end and thus a tangent to the guiding surface at the rear end is at a preferred angle between 60° and 100° to a tangent formed at the front end of the guiding surface, wherein the two tangents therein are viewed in a plane, which is perpendicular to the longitudinal axis of the injector device. If the guiding surface located between the two ends is correspondingly continuously and steplessly bent and in particular then also bent only in one direction and thus having a direction of curvature, thus, the steep turn-like guiding surface is correspondingly further specified at the rear section.

At least one closing tip includes a top side in the mentioned advantageous implementation, which adjoins to the upper edge of the guiding surface. The top side is preferably flatly formed. Moreover, a closing tip also includes an outer side, which also adjoins to the guiding surface and also adjoins to the top side and is also substantially preferably flatly formed. A bottom side is formed opposing, which extends substantially in a front section of the closing tip, wherein this bottom side is preferably also formed in curved or arc-shaped manner. In this context, the curvature is also preferably formed in the direction towards the top side and the outer side and thus preferably convex.

In particular, it is provided that the steep turn-like rear section has a thin rear end, which continuously widens up to a middle thickness and then again continuously thins from the middle thickness to a front end of this rear section. Such a specification describes the area geometry of the guiding surface again more specifically. By this configuration, the above mentioned advantages with respect to improved guidance and continuous pivoting of the cover flaps with the required supporting function of the closing tips are again improved.

On the other hand, especially by the thinnings at the ends and thus the also tapering area ends of the guiding surface, a very small-area contact with the outer sides of the cover flaps is achieved in the front-side first contact on the one hand, such that here high frictions or mechanical expansions first cannot occur. With the then increasing guiding surface, the mechanical contact and the abutment between the guiding surface and the cover flaps is increased such that the guiding behavior and the stabilization are improved.

Preferably, it is provided that the steep turn-like rear section joins to a front section of the guiding surface extending parallel to the longitudinal axis. By this separation into at least two sections of the guiding surface, the already above mentioned very different functionalities can be achieved. By exactly this arrangement in axial direction, the respectively required functions are very exactly achieved with respect to the mechanical requirements and also with respect to the temporal phases, in which they are substantially required if the axial displacement of the mentioned components is effected in a certain temporal sequence to each other and for a certain period of time.

Preferably, it is provided that a guiding surface has a rear section, which has a first S-shaped extension of a top side viewed in a vertical sectional plane. In this alternative configuration of the shape of the guiding surface, the already above mentioned advantages are also achieved. Therein, the sectional plane is oriented in the direction of the longitudinal axis or parallel thereto. By this shaping of the closing tip in a very specific direction and on a very specific side of the overall geometry, the advantageousness, as it was explained above, is also achieved by a different concept.

Preferably, it is provided that the guiding surface has a second S-shaped extension in the rear section in this further implementation, which is located deeper at least in certain areas viewed over its length in the direction of the longitudinal axis than the first S-shaped extension. Such a configuration allows a jerk-free relative displacement of the closing tip to the cassette to each other in axial direction, however it allows high guiding functionality and stabilization in lateral direction thereto on the other hand. Moreover, the pivoting behavior of the cover flaps of the cassette is particularly favored and supported.

Preferably, it is provided that the second S-shaped extension on a closing element or on a closing tip is disposed facing the other opposing closing tip and closer thereto than the first S-shaped extension of a closing tip. This second S-shaped extension is therefore closer to the longitudinal axis than the first S-shaped extension viewed perpendicular to the longitudinal axis of the injector device. Especially by this specific positioning, the above mentioned advantages with respect to the lateral stabilization and the guidance are favored.

Preferably, it is provided that a transition between the first and the second S-shaped extension is formed in stepped manner at least in certain areas. Such a discrete transition configuration allows configuring and keeping the axial displacement with lateral stabilization in rail-like manner to a special extent.

Preferably, it is provided that the guiding surfaces of the closing tips each have a front section, wherein a guiding slit for guiding in axial direction is formed for cover flaps of the cassette at least between the front sections.

The advantages to be achieved in this respect are already above explained in detail. Especially in the above mentioned first embodiment of the specific shape of the rear sections of the closing tips, the width of this guiding slit viewed perpendicular to the longitudinal axis is smaller than the distance between the rear sections of the guiding surface. By such a narrow guiding slit, an in particular also exactly fitting guidance for the closed cover flaps can be allowed with further axial displacement relative to the closing tips such that unintended partial reopening of the cover flaps is prevented and moreover entire rotation of the cassette around the longitudinal axis is also prevented. The position of the intraocular lens, as it is achieved in this pre-folded state in the cassette before introduction into the guide channel of the injector tip, is therefore maintained unchanged and exact in position. The further folding in the guide channel of the injector tip itself can then be continued as desired and exactly that final folding of the lens is achieved at the outlet of the guide channel as it can then be optimally introduced into the eye, in particular to be able to achieve an introduction capable of small incision.

Preferably, it is provided that the closing tips extend into an in particular groove-like receiving space for the cassette formed in an injector tube adjoining to the injector tip and join to an inner side of a front bounding wall of the receiving space. By such a configuration, the closing tips are mechanically stably fixed on the one hand, recessed to a certain extent and disposed in protected manner on the other hand. Undesired hitting by other components can thereby be prevented such that bending or breaking of the closing tips can be prevented.

Preferably, it is provided that the closing tips are formed integrally with the injector tip. Preferably, an integral configuration of the closing tips with the injector tube can also be provided. In particular, the closing tips are each integrally formed of plastic and in the integral configuration with the injector tip and/or the injector tube, an integral body is then also respectively formed.

Preferably, it is provided that the injector device has a cassette for receiving the intraocular lens, wherein the cassette includes a base part, on which the cover flaps are disposed pivotable around the longitudinal axis of the injector device relative to the base part. By these wings or cover flaps, a particularly simple and easily accessible introduction of the intraocular lens into the cassette can be allowed and moreover the further pre-folding in the cassette can also be effected in particularly suitable manner.

In particular, the intraocular lens is then already disposed in the cassette.

The cassette can be formed such that it is a separate module, which can be mechanically attached to the injector device by a user, in particular by medical personnel. However, it can also be provided that the cassette is already attached to the injector device and is correspondingly delivered to the medical personnel from the manufacturer of the injector device.

Preferably, the cassette is also integrally formed, in particular of plastic. In this context, it is advantageous if the base part is connected to the cover flaps via swing hinges, which can be film hinges in an advantageous implementation.

In a preferred implementation, it is provided that the cover flaps are formed bent or curved at least in certain areas.

Preferably, it is provided that the injector device has an in particular groove-like receiving space for the cassette formed in an injector tube adjoining to the injector tip, which includes at least one axial guiding track, by which a relative movement between the guiding tube and the cassette is axially guided. Thereby, the relative movement is preset and kept in a well defined manner.

Preferably, the guiding track is a slit or a groove or an aperture on a bottom of the injector tube. Since the injector tube is intrinsically very stable, it is particularly advantageously suitable as a support for the cassette and also allows in this context that the guiding track is maintained very linearly and does not twist. The axial displacement is thereby allowed in much defined manner and without jerk. Clamping or spreading is prevented. Further, an integrated configuration of the guiding track saving installation space is thereby achieved.

It is particularly advantageous if the injector device has a support slide and the cassette with the intraocular lens is received in the support slide. Thereby, the cassette, which is optionally constructed slightly more filigree, and in particular if the cover flaps are intrinsically bendable, a robust, mechanically stable component is provided by the support slide on the one hand, which advantageously allows the reception on the one hand and the movement of the cassette on the other hand. The mechanical interaction with other components of the injector device is then achieved via the support slide and in particular the axial relative movement to the injector tube and the closing tips is specially guided by this support slide.

Preferably, the support slide is formed with a geometry, which is formed very warp resistant such that the above mentioned advantages are favored. Preferably, the cassette is completely received in the interior of the support slide such that the cassette is circumferentially protected, but is accessible on the front side and from the rear on the other hand.

Preferably, it is provided that the support slide is tubularly formed and the cassette is disposed in the interior of the support slide in particular in positionally fixed manner. Thereby, the above mentioned advantages can be achieved to particular extent. Preferably, the support slide is disposed in the receiving space of the injector device such that here too it can be embedded to a certain extent and positioned in laterally supported manner and from below.

Preferably, it is provided that a relative movement between the injector tube and the cassette is axially guided. Thereto, the support slide is correspondingly coupled to the injector device, in particular the injector tube.

In a preferred implementation, it is provided that the support slide is positioned in the receiving space rearward spaced to the closing tips in its non-displaced base position. In this context, the receiving space is advantageously dimensioned such that the closing tips and this support slide can virtually be disposed in series to each other viewed in longitudinal direction of the injector device. Thus, a very simple and user-friendly loading of the receiving space with the support slide can be allowed on the one hand, the accessibility both to the closing tips and to the support slide is possible in unrestricted manner on the other hand. Moreover, especially by such a dimensioning of the receiving space and the desired scenario of the relative axial displacement between the closing tips and this support slide with the cassette is maximally accounted for and the movement scenario of the cover flaps much defined by the specific shaping of the closing tips in axially displacing the components to each other can thereby fully be asserted.

Preferably, it is provided that the support slide has a handle element, which can be gripped by a user, wherein the support slide with the cassette is axially displaceable to the front end of the receiving space in user-guided manner relative to the other components of the injector device. In such a configuration, the injector tube is fixedly connected to a piston tube of the injector device, wherein the piston tube in the push-out piston, by means of which the intraocular lens is shifted from the cassette into the injector tip, in particular the guide channel. In this configuration, thus, axial relative displacement between the components is achieved in that only the support slide with the cassette is moved and axially displaced.

In an alternative configuration, it is provided that the support slide is disposed positionally fixed on a piston tube of the injector device and an injector tube of the injector device having the receiving space, on which the injector tip is disposed, is axially displaceable relative to the piston tube with the cassette. In this configuration, thus, the support slide with the cassette is not actively displaced, but the injector tube is virtually displaced relative to the piston tube by a user.

Preferably, it is provided that the support slide has guiding blades on its bottom, which engage with a guiding track in the injector tube. By such a configuration, a very simple mechanical coupling between the support slide and the injector tube can be allowed and the axial movement guidance can be very simply effected. Moreover, undesired movement in a direction lateral or oblique to the longitudinal axis is prevented.

Preferably, the guiding blades are formed as flexible locking elements. These locking elements, which can also be formed as snap-in elements, allow simple and secure mechanical coupling of the components and engage behind the guiding track. In this context, it is advantageous if the guiding track is an aperture or a slit such that these guiding blades in the form of the locking elements extend through the guiding slit and virtually come to lie then encompassing the edge of the slit at the outside. The above mentioned advantages are thereby particularly favored.

Preferably, it is provided that an engaging space for the closing tips is formed between an inner wall of the support slide and outer sides of pivotable cover flaps of the cassette. By this configuration, sufficient movement of the cover flaps for pivoting thereof is allowed on the one hand and yet suitable guidance of this pivoting is achieved on the other hand.

Preferably, it is provided that the closing tips and the cassette are disposed such that in an axial relative displacement between the cassette and the closing tips, the closing tips contact outer sides of opened cover flaps, and in further axial displacement between the cassette and the closing tips relative to each other, the cover flaps are automatically pivotable around the longitudinal axis of the injector device and closable by the closing tips. The advantages achieved therein are already above extensively explained.

Preferably, it is provided that a top ceiling side of an inner wall of the support slide is formed curved, in particular dome-like formed, and a radius of the curvature is larger than a radius of the curvature of the cover flaps at least in certain areas. Thereby, closing of the cover flaps can be effected in unimpeded and in desired manner.

In particular, it is provided that the cover flaps in pivoting around the longitudinal axis of the injector device abut on the ceiling side during the pivoting operation at least in certain phases or temporarily and thereby are intrinsically bendable. Especially in the configurations, in which the cover flaps are intrinsically deformable, this can be provided. This intrinsic bending in closing is therefore performed in correspondingly defined manner. This defined performing is therefore effected both with regard to the degree of the bending and with regard to the point of time, at which the bending is to be effected during pivoting of the cover flaps. The scenario induced with regard to the degree and/or the point of time of deformation is thereby automatically performed.

Preferably, it is provided that hammerhead-shaped or hammerhead-like thickenings at free ends of the cover flaps are contacted only with outer ends of the contact surfaces of the hammerhead-like thickenings in pivoting by the intrinsic bending of the cover flaps, in particular of arc-shaped flap sections. Thus, first, a linear or very small-area mechanical contact between the thickenings is achieved. This is particularly advantageous to cause a defined movement scenario of the intrinsically bent cover flaps in the further closing operation such that they again assume their non-deformed basic shape and then the defined completion of the pre-folding of the intraocular lens in the cassette can also be specifically effected in this operation.

Preferably, the cover flaps and the thickenings are formed such that the contact surfaces of these hammerhead-like thickenings lean to each other in further pivoting around the longitudinal axis into the closed final position of the cover flaps and thereby the intrinsically bent state of the cover flaps is automatically returnable into the base position. The base position is provided with arc-shaped flap sections in this context, but which are then less severely bent than in the intrinsically bent state.

In a preferred implementation of the cassette, it is provided that it has an upward pivotable securing cover for the lens besides the cover flaps. The securing cover is therefore an additional further component besides the cover flaps. Upward falling out or undesired forward slipping in the direction of the longitudinal axis is thereby prevented.

Preferably, the securing cover is relatively pivotable with respect to the base part of the cassette. In particular, the securing cover is connected to the base body or the base part via a film hinge and upward and downward pivotable relative thereto.

Preferably, the securing cover has a hook-shaped securing bracket extending forwards. The above mentioned advantages are thereby particularly achieved and the cover flaps are not restricted with respect to their shaping and local positioning in the opened state.

Preferably, it is provided that the securing cover is closed in the opened state of the cover flaps.

In a particularly preferred implementation, it is provided that the securing cover has lifting elements, in particular lifting flanks, which in closing the cover flaps and thus in pivoting thereof around the longitudinal axis of the cassette are contacted by them and automatic opening of the securing cover can be performed in further closing of the cover flaps.

Furthermore, the invention relates to a method for folding an intraocular lens in a cassette, which is formed for disposing in an injector device for introducing an intraocular lens into an eye, wherein two cover flaps disposed on a base part of the cassette are pivoted around a longitudinal axis of the cassette for closing the cassette and the cover flaps additionally are intrinsically bent towards the intraocular lens in closing such that the intraocular lens is pre-folded in the cassette by pivoting the cover flaps and the intrinsic bending. The advantages achievable thereby are already mentioned above.

Preferably, in displacing the cassette in axial direction relative to the closing tips, engaging of the closing tips between a support slide and the cassette received in the carrier slide is achieved. The closing tips abut on outer sides of the cover flaps with guiding surfaces and by the shaping of the guiding surfaces, in further exclusively axial displacement between the closing tips and the cassette, transition of the cover flaps into their closed final position is performed. Alone by the exclusively axial relative displacement between the closing tips and the cassette, the cover flaps of the cassette are automatically pivoted around the longitudinal axis and closed. In particular, further guiding of the closed cover flaps in a guiding slit between the closing tips is performed. This is preferably effected until a final position between the cassette and an injector tube of the injector device is achieved, and then subsequently the intraocular lens is shifted out of the cassette into the injector tip or the guide channel thereof.

Further advantageous implementations of the method according to the invention are constituted by advantageous implementations of the injector device or the cassette. The objective features mentioned hereto in the injector device and the cassette serve individually or in combination for realizing corresponding method steps.

With respect to the terms of "rear" or "front", this is defined to each other viewed in the direction of the longitudinal axis and with regard to the injector tip.

Furthermore, the invention relates to a packaging and transport device for an intraocular lens. The device includes a transport container and an injector device according to the invention or an advantageous configuration thereof. The injector device can be introduced into the transport container, and in particular in the finished state of the packaging and transport device, the injector device is positionally stably disposed in the transport container. In this final state of the packaging and transport device, an intraocular lens is disposed in the injector device. In this packaging and transport device for an intraocular lens, the already above mentioned advantages clearly take effect. Besides improved operability, the damage of the intraocular lens can be reduced. Moreover, additional auxiliary tools such as for example tweezers or the like are not required to remove the intraocular lens from the transport container in required use in a surgical procedure.

Preferably, a sterile liquid is contained in the transport container, in which the lens is immersed disposed. After packaging and thus also in the transport, the lens is surrounded by this sterile liquid such that undesired contaminations can be avoided here too. In particular, the transport container is closed with a covering on a top side such that here too contaminations cannot enter the receiving space of the transport container. Moreover, shipping is possible without liquid loss in this respect.

Preferably, a sterile and germ-free closure of the transport container is ensured by the covering. Thus, adherence of the covering or thermally welded connection can be provided here. Thus, the transport container is completely closed for storage and for transport. The covering can be transparently formed at least in certain areas such that the retaining device and also the intraocular lens in the transport container can be seen. Information about parameters characterizing the intraocular lens can be indicated on the covering.

Overall, by the packaging and transport device and the injector device, an overall system is provided, which ensures a highly functional procedure from the production and packaging of the lens up to insertion of the lens into the eye. This is improved in particular with regard to the compliance with the sterilization operations and the germ-free treatment of the lens as well as with regard to the user-friendly operability and coordinated sequences in the use of the lens. If such a lens is virtually used in a surgical procedure and the packaging and transport device of the intraocular lens according to the invention or an advantageous configuration thereof is already delivered to the medical personnel, thus, only the packaging has to be opened by removing the covering from the transport container. The medical personnel only have to remove the injector device from the transport container and perform the explained initial movements to be able to achieve the further automatic loading of the injector tip with the lens.

In that at least one of the front-side openings of the receiving container is closed by a very thin foil, it can be allowed that the intraocular lens is already directly introduced into the cassette and the cassette is therefore formed in multifunctional manner. This, since it thus also has the integral function of the transport container. The cassette according to the invention is therefore a component, which constitutes the transport container itself on the one hand, also exactly constitutes the component on the other hand, which is connected or can be connected to the injector device and which then allows in the state connected to the injector device that the intraocular lens located therein can be shifted out of the cassette. By the foil, mechanically stable closure is also allowed, which also allows the sterile storage of the intraocular lens in the cassette on the other hand.

Preferably, a balanced salt solution or pure water is disposed in the interior of the receiving container. The intraocular lens located therein is thereby stored in sterile manner.

By the attachment of a foil to at least one of the front sides, this foil can also be processed in simple manner low in effort to then be able to subsequently output the intraocular lens from the receiving container. This in particular if this intraocular lens is to be shifted out of this cassette by a piston of the injector device.

In particular, thus, after completion of the cassette, the intraocular lens is introduced into the receiving container and the balanced salt solution. Thereafter, at least one of the openings is closed by the foil. The cassette thus provided therefore includes a hermetically closed receiving container, in which the intraocular lens is already stored and integrated in sterile manner. A cassette thus formed can then furthermore already be integrated in an injector device such that the complete injector device can already be provided and subsequently then be delivered and optionally delivered to a surgeon. In such a configuration, thus, the amount of work and in particular the assembly effort is minimized.

It is particularly advantageous if a foil is a coextruded foil. For such a specific foil, it is possible in a manner to be particularly emphasized that a hermetically tight seal of the opening with the foil can be ensured on the one hand. On the other hand, thereby, it is achieved that a particularly sterile barrier is also generated by the foil such that undesired contaminations cannot enter the interior of the receiving container. Moreover, this coextruded foil also ensures the desired flexibility with regard to the subsequent removal or piercing when the intraocular lens is to be shifted out of the cassette.

It is advantageous that the coextruded foil has an aluminum layer. Herein, aluminum is a material to be particularly emphasized to be able to achieve the sterile barrier of the foil.

Advantageously, it is provided that the coextruded foil has propylene, in particular includes a polypropylene layer. In particular, this material component is suitable for hermetically sealing and attaching to the receiving container. Therein, the polypropylene material can be connected to the material in the receiving container in particularly sealing manner.

Preferably, the coextruded foil is formed to the effect that it has a polypropylene ply, on which an aluminum ply is formed. The aluminum ply is then preferably also covered by a varnish or other coating.

Preferably, it is provided that a foil is formed two-ply on an opening. This is in particular conceived to the effect that the ply closer to the receiving container is fixedly connected thereto such that the sealing and sterile barrier is ensured. The second ply facing away from the receiving container is in particular conceived to the effect that it is in particular not fixedly connected to the first ply in the overlap area with the first ply. Thus, a certain relative movability to the first ply is ensured.

In particular, the cassette can be a receiving container for storing a hydrophilic lens in a water medium (pure or salty water).

Preferably, it is provided that the cassette is steam sterilized and the injector tip and the injector tube are sterilized by ethylene oxide.

BRIEF DESCRIPTION OF THE DRAWINGS

The invention will now be described with reference to the drawings wherein:

FIG. 5 is a perspective representation of an embodiment of a cassette according to the invention for receiving an intraocular lens with an additional support slide;

FIG. 6 is a further perspective representation of the device according to FIG. 5;

FIG. 7 is a perspective sectional view of the device according to FIG. 5 and FIG. 6;

FIG. 21 is a plan view of a partial section of the injector device according to FIG. 19 with closing tips shown from above;

FIG. 22 is a perspective representation of the components in FIG. 21;

FIG. 23 is a side view of partial components of the representation in FIG. 21 and FIG. 22;

FIG. 24 is a plan view of the representation in FIG. 23;

FIG. 28 is a perspective representation of an embodiment of a device including a support slide and a cassette for an intraocular lens;

FIG. 29 is a further perspective representation of the device according to FIG. 28 without end-side covering elements;

FIG. 30 is a perspective representation of the device according to FIG. 29 in a state received in an injector tube of the injector device;

FIG. 31 is a front view of the representation in FIG. 30;

DESCRIPTION OF THE PREFERRED EMBODIMENTS OF THE INVENTION

Figure 1:
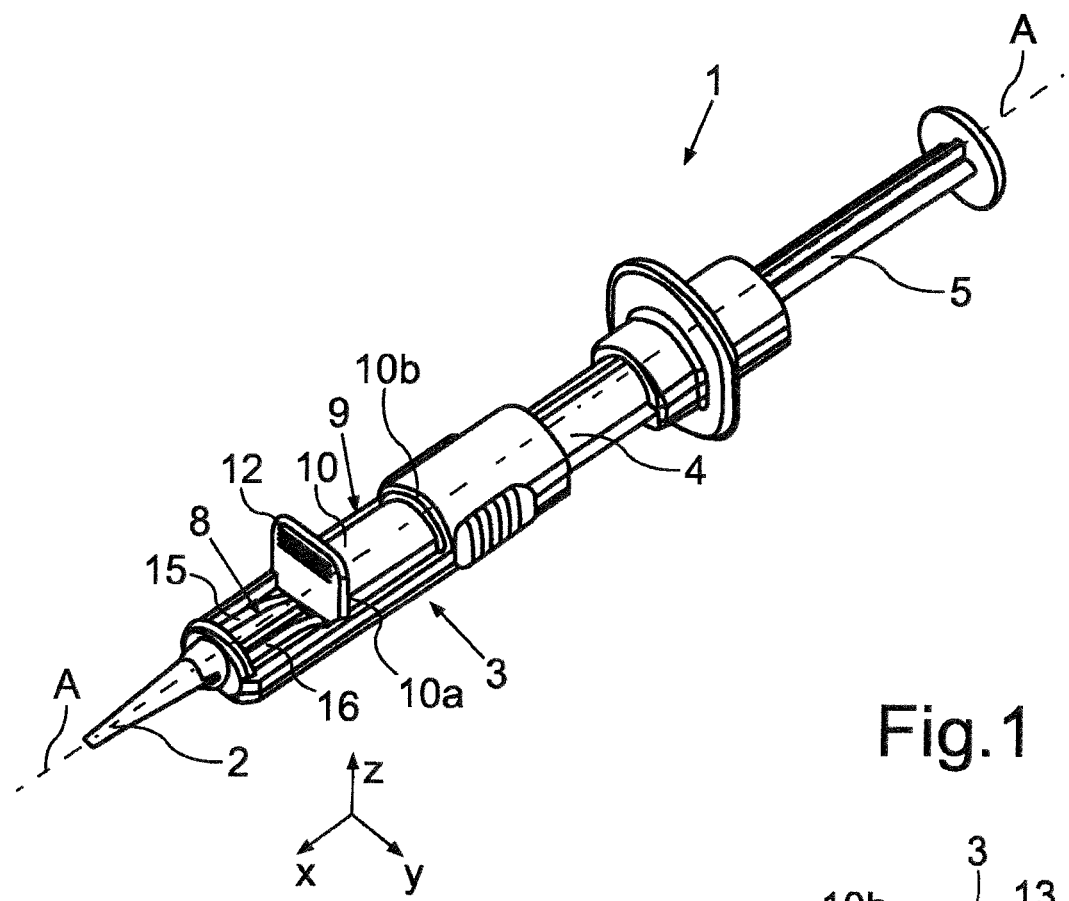
FIG. 1 is a perspective representation of an embodiment of an injector device according to the invention.

In FIG. 1, an embodiment of an injector device 1 is shown in a perspective view, which is formed for introducing an intraocular lens into an eye. In the shown implementation, the injector device 1 includes an injector tip 2 connected to an injector tube 3. The injector tube 3 is displaceable in the direction of a longitudinal axis A of the injector device 1 relative with respect to a piston tube 4. The piston tube 4 is provided for receiving a piston 5, which is displaceable in axial direction. The intraocular lens is pushed out of a cassette 6 (FIG. 2) and displaced into a guide channel 7 (FIG. 2) of the injector tip 2 by the piston 5.

As is apparent in FIG. 1, the injector tube 3 has an upwards open receiving space 8, which is formed for receiving a device 9. The device 9 includes the cassette 6 and a support slide 10. In the shown implementation, the support slide 10 is formed as an integral tubular component. In the interior 11 (FIG. 2), the cassette 6 is stationarily positioned to the support slide 10.

The receiving space 8 has an axial length (x-direction), which is greater than a length of the device 9 and thus also greater than the length of the support slide 10. As can be taken from the representations in particular in FIG. 1 and FIG. 2, the cassette 6 is completely received in the interior 11 and does not extend beyond the dimensions of the support slide 10 in axial direction.

In the shown implementation in FIG. 1, the support slide 10 is closed with a covering element at a front end 10a. Above and below, the indications to "front" and "rear" components relate to their position in the direction of the longitudinal axis A with regard to the injector tip 2 of the device 1. The covering element 12 can be plate-like and intrinsically rigidly formed. However, it can also be a foil, for example a coextruded foil. However, it can also be a foil, on which a rigid element for gripping is disposed, by which the foil can then be peeled off.

At a rear end 10b, the support slide 10 is fixedly connected to the piston tube 4. As it is in particular apparent thereto in FIG. 2, the piston tube 4 is internally hollow and the piston 5 is axially displaceable biased by a spring 13.

The injector tip 2 includes the already mentioned guide channel 7, which has a rear inlet 7a and a front outlet 7b. The rear inlet 7a is disposed facing the receiving space 8 and the intraocular lens 14 (FIG. 2) pushed out of the cassette 6 can be pushed into the guide channel 7 via this rear inlet 7a. The front end and thus the front outlet 7b can be introduced into a small incision in the eye to be operated and thereto the intraocular lens 14 can be pushed into the eye from the injector device 1.

Figure 2:
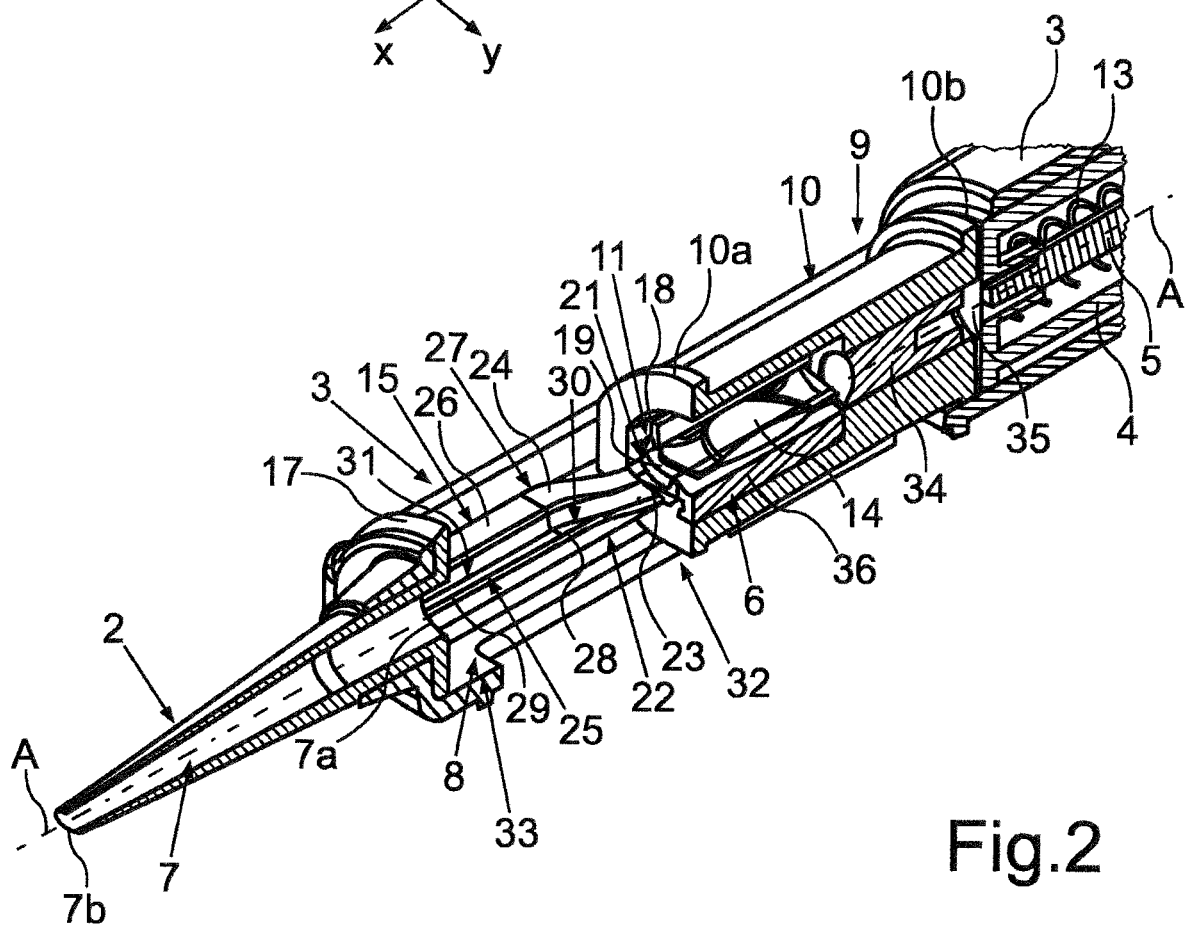
FIG. 2 is a partial representation of the injector device according to FIG. 1 in perspective sectional view.

As is apparent from the representation in FIG. 1 and FIG. 2, the guide channel 7 tapers viewed from its rear inlet 7a to its front outlet 7b, wherein this is in particular continuously effected.

As is shown, the injector device 1 includes two closing tips 15 and 16. These closing tips 15 and 16, which can also be referred to as closing prongs or closing blades or closure fingers, extend parallel to each other and spaced to each other with respect to the longitudinal axis A. With regard to the longitudinal axis A, the two closing tips 15 and 16 are positioned symmetrically opposite thereto and formed symmetrically to each other. As is apparent from the representation in FIG. 1 and FIG. 2, the closing tips 15 and 16 extend in the receiving space 8. They join to a front bounding wall 17, which delimits the receiving space 8 on the front side. The bounding wall 17 is configured integrally with the injector tip 2 in the shown implementation. The closing tips 15 and 16 are configured for closing cover flaps of the cassette 6 when an axial relative displacement between the closing tips 15 and 16 of the cassette 6 is effected.

As is shown in the operating state in FIG. 1 and FIG. 2, the device 9 with the support slide 10 and the cassette 6 is positioned at the rear end of the receiving space 8 and thus a positional initial state is occupied. In this position, in particular, contact between the closing tips 15 and 16 and the cassette 6 does not yet exist.

The closing tips 15 and 16 are analogously formed such that the following explanation to the closing tip 15 as it is illustrated in FIG. 2 in enlarged manner also applies to the closing tip 16.

The closing tips 15 and 16 extend further rearwards than the rear inlet 7a of the injector tip 2 viewed in axial direction.

As is in particular apparent in FIG. 2, the cassette 6 is positioned in the interior 11 such that an engaging space 21 is formed between an inner wall 18 of the support slide 10 and the cover flaps 19 and 20 (FIG. 5) of the cassette 6. The closing tips 15 and 16 engage with this engaging space 21 if an axial relative displacement between the closing tips 15 and 16 and the device 9 is effected.

The closing tip 15 includes a rear first length section 22, which tapers to a rear end 23 of the closing tip 15. A top side section 24 of a top side of the first rear section 22 is configured with a first S-shaped extension, wherein this first S-shaped extension is formed in a sectional plane extending in the x-z plane. This ramp-like rise with the first S-shaped extension then transitions into a front second length section 25 of the closing tip 15 in a flatly configured top side section 26. By the top side sections 24 and 26, a part of a guiding surface 27 is formed. The guiding surface 27 complements itself afterwards by a second S-shaped extension of a top side sections 28 in the first rear section 22. This second S-shaped extension is also to be understood in a sectional plane, which extends in the x-z plane.

As is apparent from the representation in FIG. 2, this second S-shaped extension of the top side section 28 then also transitions into a flat top side section 29 in the front second length section 25 of the closing tip 15.

As is apparent thereto in FIG. 2, in height direction and thus in z-direction, the second S-shaped extension and thus the top side section 28 is located deeper than the top side section 24. Similarly, the top side section 29 is located deeper than the top side section 26. Thus, the guiding surface 27 is especially constituted by the top side sections 24, 26, 28 and 29.

Between the top side sections 24 and 28, a stepped transition 30 is at least partially formed viewed over the length and thus over the extension in x-direction. Correspondingly, a stepped transition 31 is also formed between the top side sections 26 and 29. As is shown according to FIG. 2, the top side sections 28 and 29 located deeper are disposed closer to the longitudinal axis A than the top side sections 24 and 26 located higher. The top side sections 28 and 29 located deeper are thus formed facing the closing tip 16.

Moreover, the injector tube 3 also has a guiding slit 32, which is formed in a bottom 33 of the injector tube 3. The device 9 is disposed engaging with this guiding slit 32 such that the axial relative displacement of the injector tube 3 relative to the device 9 and to the piston tube 4 is correspondingly guided and laterally stabilized.

Figure 3:
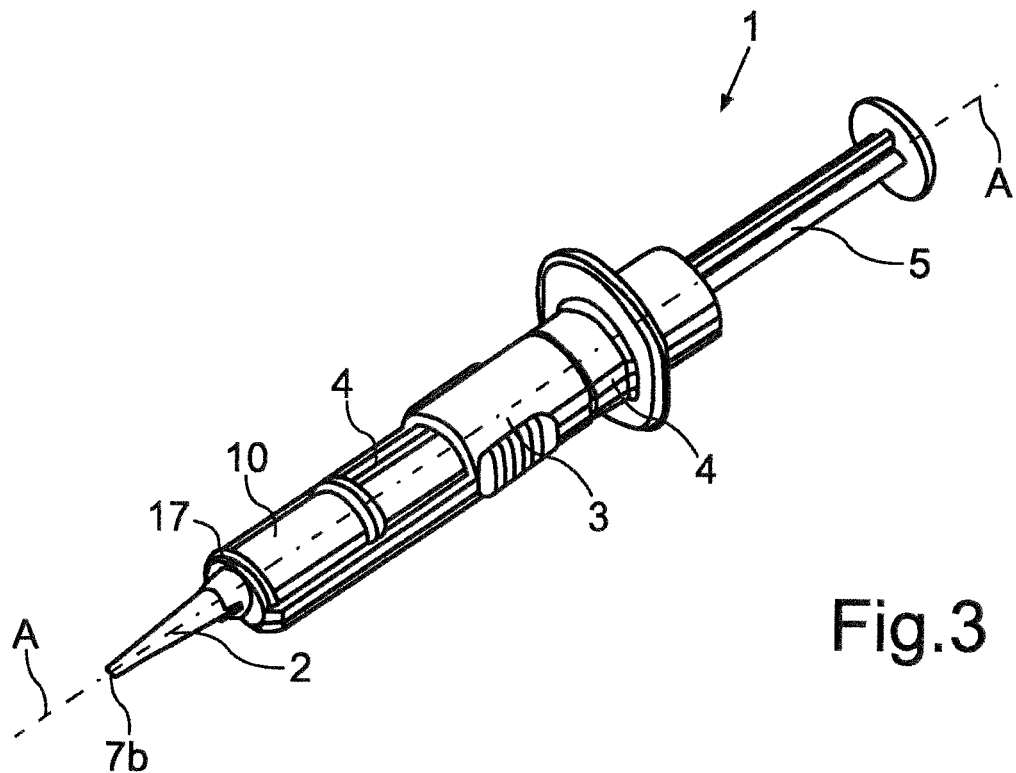
FIG. 3 is the injector device according to FIG. 1 in an operating state different from FIG. 1.

In FIG. 3, the injector device 1 is shown in an operating state different from FIG. 1 and FIG. 2. In contrast to FIG. 1 and FIG. 2, here, the completely shifted-back state of the injector tube 3 relative to the piston tube 4 is illustrated. In this configuration, the device 9 with the support slide 10 is therefore especially disposed abutting on the delimiting or bounding wall 17. In this implementation, the closing tips 15 and 16 are positioned maximally shifted into the interior 11.

Figure 4:
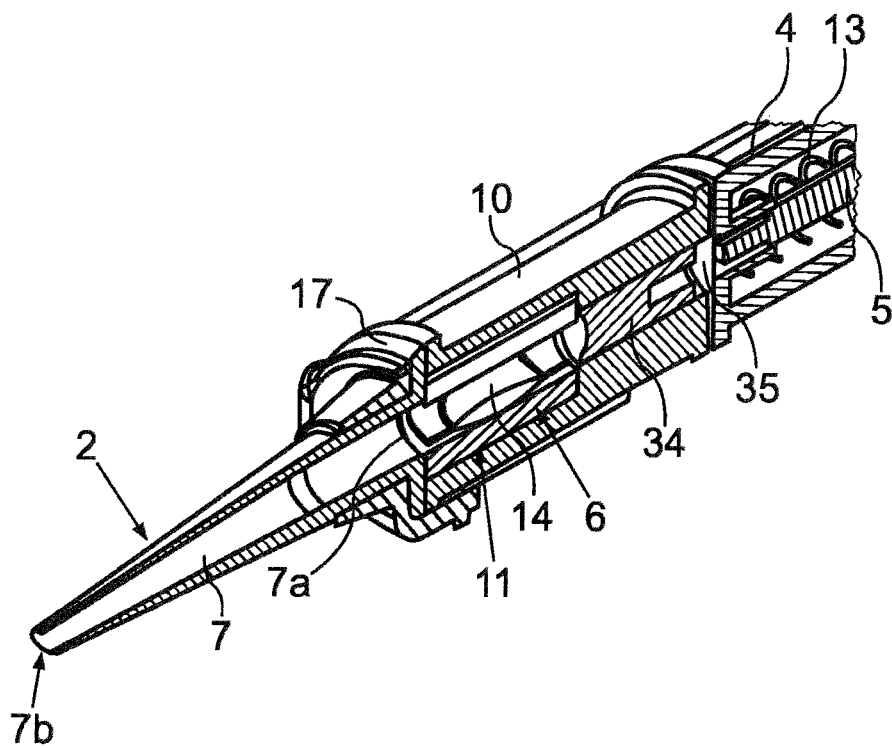
FIG. 4 is a partial representation of the injector device according to FIG. 3 in perspective sectional view.

Due to the shaping of the closing tips 15 and 16, on this movement path between the operating states according to FIG. 1 and FIG. 2 on the one hand and FIG. 3 and FIG. 4 on the other hand, by this axial relative displacement, movement of the cover flaps 19 and 20 of the cassette 6 about the longitudinal axis A is automatically effected such that they are transitioned starting from the completely opened state shown in FIG. 2 into the completely closed state shown in FIG. 4 and this is automatically effected.

Thereby, the intraocular lens 14 first preferably stored in the non-deformed state in the cassette 6 is positioned in the desired pre-folded final position in the cassette 6 in the operating state according to FIG. 3 and FIG. 4. As is shown in FIG. 2 and FIG. 4, the support slide 10 includes a channel in the rear area, in which a shift-out element 34, which is preferably formed of an elastically deformable material, is disposed. This component also referred to as damping element is shifted into the interior 11 by the piston 5 while shifting the intraocular lens 14 out of the cassette 6 such that the piston 5 does not directly come into contact with the intraocular lens 14. This affords advantages to the effect that the very hard and stiff piston 5 then does not cause mechanical damage to the intraocular lens 14.

As is shown in FIG. 2 and FIG. 4, a covering element 35 is also disposed at the rear end 10b, which can also be a foil. This covering element 35 is then pierced by the piston 5 and the shift-out element 34 is shifted into the interior 11. However, according to the representation in FIG. 4, this is only effected if the operating state according to FIG. 3 and FIG. 4 is achieved on the one hand and then the piston 5 is shifted forward in axial direction.

Moreover, in FIG. 2 and FIG. 4, a base part 36 of the cassette 6 is also apparent, which is fixedly connected to the support slide 10. Thereto, a configuration T-shaped in cross-section of the base part 36 is for example formed such that certain anchoring of the cassette 6 in the support slide 10 is achieved. The two cover flaps 19 and 20 are disposed on this base part 36 pivotable relative thereto. In particular, the cassette 6 is integrally formed of plastic and the cover flaps 19 and 20 are disposed thereon via film hinges 37 and 38 (FIG. 5).

In FIG. 4, the final pre-folded state of the intraocular lens 14 in the cassette 6 is shown, before this intraocular lens 14 is then subsequently shifted into the guide channel 7.

In FIG. 5, a perspective representation of an embodiment of the device 9 is shown. The tubular or annular configuration of the support slide 10 is illustrated. Moreover, guide blades 39 formed on a bottom side 40 of the support slide 10 are also shown. By means of these guide blades 39, the engagement with the guiding slit or guide track 32 is provided.

In FIG. 6, a further perspective representation of the device 9, as it is shown in FIG. 5, is illustrated. The cover flaps 19 and 20 are shown in a completely opened state. The inner wall 18 of the support slide 9 delimiting the interior 11 includes a dome-like or curved ceiling side 41 such that a tunnel is formed.

In the shown embodiment, the cover flaps 19 and 20 are intrinsically deformable. Especially, the deformation is effected in a defined manner and thus in a directed and autonomous manner by the closing operation. In a non-deformed base position, these cover flaps 19 and 20 have, as it is shown in FIGS. 5 to 7, an arc-shaped flap section 42. At a front free end 43 of this arc-shaped flap section 42, a hammerhead-shaped thickening 44 is formed. This is realized in the cover flap 20 in analogous manner.

The cover flaps 19 and 20 have outer sides 19a and 20a. They are not straight, but formed with different curvatures. This arises by different radial thicknesses of length areas of the cover flaps in their lengths viewed in the direction about the axis A. Thereto, the cover flaps have thinner flap sections 42 and 47 besides the end-side hammerhead-shaped thickenings 44 and 45, to which thicker areas then again adjoin as outward formed risers or elevations 19b and 20b on the other hand. The flap sections 42 and 47 are intrinsically reversibly bendable in repeated manner perpendicular to the axis A, but can also be formed only for defined onetime and thus plastic deformation.

In particular, the base part 36 is rigid and not deformable about the longitudinal axis A. The intrinsic deformability of the cover flaps 19 and 20 means that they can non-destructively deform their arc-shaped structure about the longitudinal axis A such that the arc shape can be enhanced or mitigated. This is effected over the entire length of the cover flaps 19 and 20 viewed in the direction of the longitudinal axis A, but for each in the same manner such that undesired twisting about the axis A is prevented.

By this possibility that the cover flaps 19 and 20 are able to intrinsically deform at least in certain areas along their lengths (measured in the cross-section perpendicular to the axis A in the direction about the axis A) in length sections perpendicular to the axis A, the pre-folding of the intraocular lens 14 in the cassette 6 is facilitated.

The procedure in this respect will be explained hereinafter.

Figure 8:
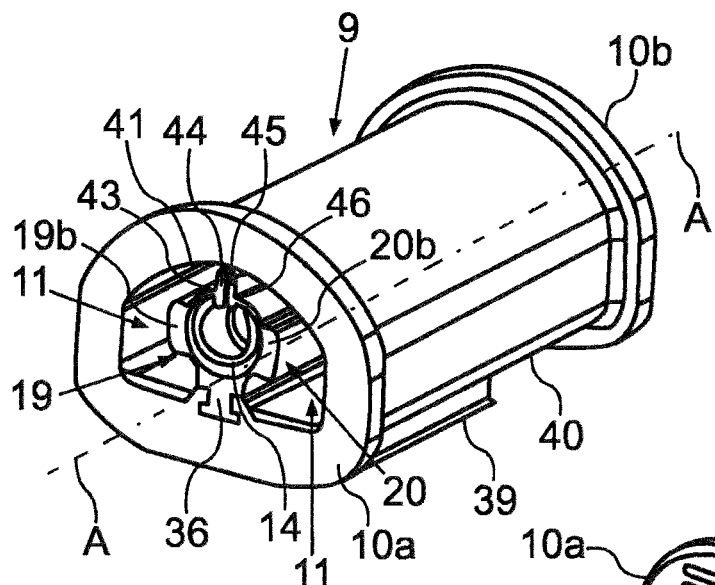
FIG. 8 is a perspective representation of the device according to FIG. 5 to FIG. 7 with closed cover flaps of the cassette.

In FIG. 8, a perspective representation of the device 9 is shown, in which the cover flaps 19 and 20 are illustrated in the completely closed state. The hammerhead-shaped thickenings 44 and 45, which is disposed at the free end 46 of the cover flap 20, is also shown.

Figure 9:
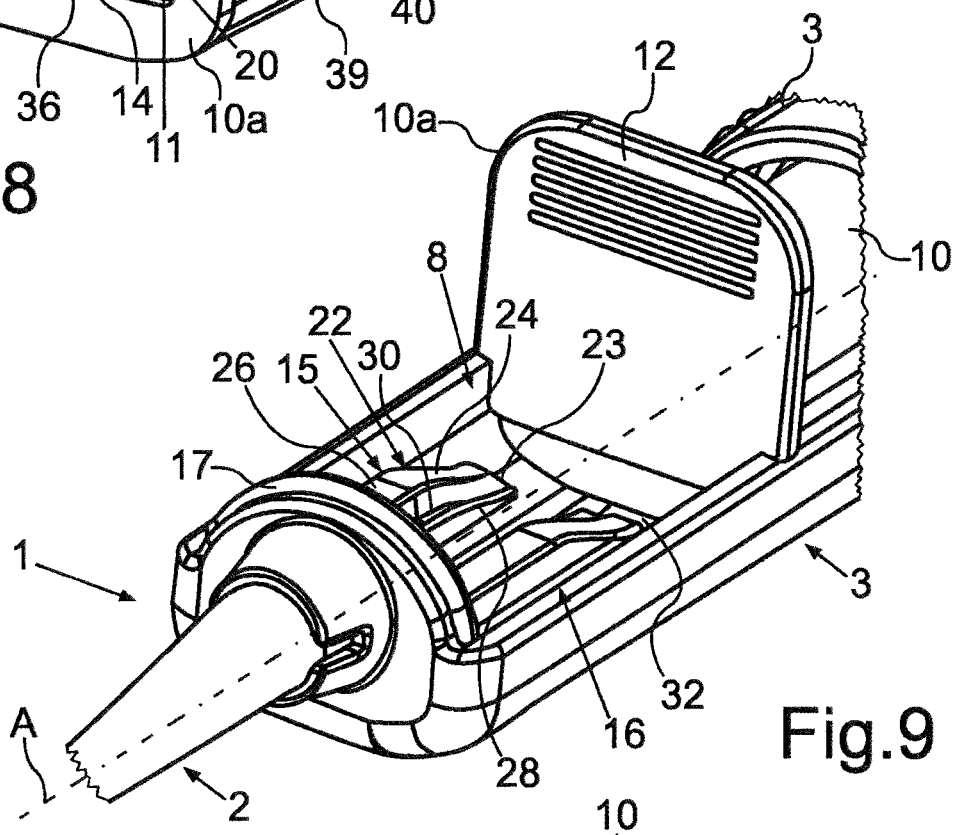
FIG. 9 is a partial representation of the injector device according to FIG. 1 in enlarged view.

In FIG. 9 an enlarged representation of a section of FIG. 1 is shown. The configuration of the closing tips 15 and 16 is apparent. Moreover, it is also apparent that the transition 30 between the top side sections 24 and 28 diminishes from the beginning of the rear section 22 up to the rear end 23 or the stepping decreases.

Figure 10:
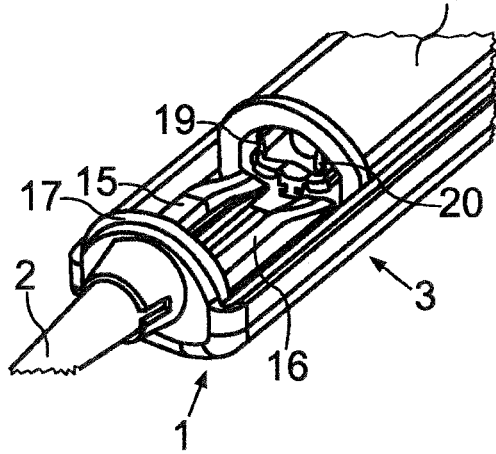
FIG. 10 is a perspective representation of a partial section of the injector device according to FIGS. 1 to 4 in a further intermediate operating state.

In FIG. 10, a representation of the section according to FIG. 9 is shown, in which a further intermediate operating state is illustrated and in which the closing tips 15 and 16 are already shifted into the interior 11 in certain areas. The contact of the guiding surfaces 27 of the closing tips 15 and 16 with outer sides (19a, 20a) of the cover flaps 19 and 20 is already effected.

Figure 11:
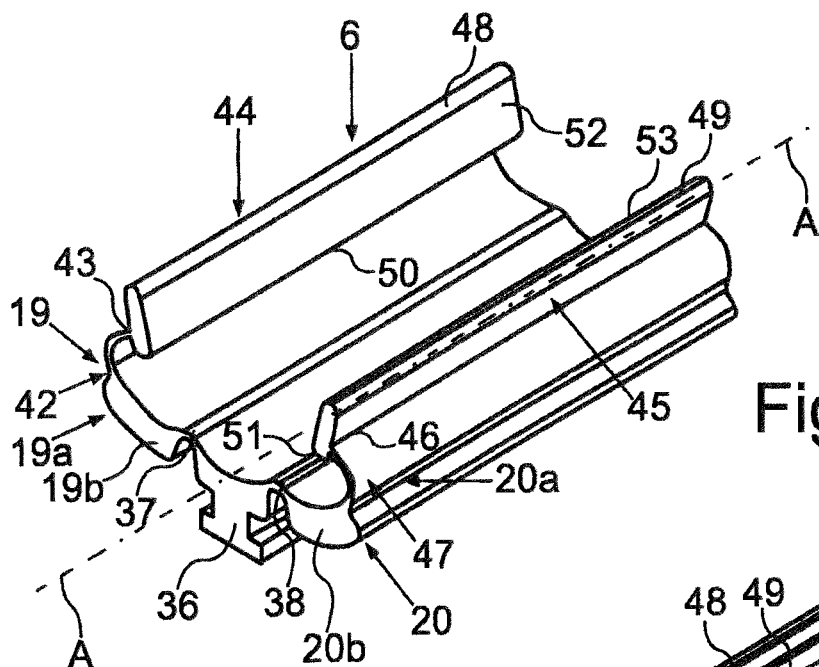
FIG. 11 is a perspective representation of an embodiment of a cassette according to the invention in the opened state of the cover flaps.

In FIG. 11, a perspective representation of an embodiment of the cassette 6 is shown, wherein here the cover flaps 19 and 20 are shown in the opened state. It is apparent that the arc-shaped flap sections 42 and 47 are deformable perpendicularly to the axis A, wherein the radial thickness thereof is smaller thus viewed perpendicular to the axis A than the radial dimensions of the thickenings 44 and 45 as well as of the risers or elevations (19b, 20b).

Moreover, the web-like thickenings 44 and 45 extend in radial direction and thus perpendicular to the axis A on both sides of the ends 43 and 46.

The two hammerhead-like or T-shaped thickenings 44 and 45 have outer ends 48 and 49 as well as inner ends 50 and 51 viewed in radial direction. Between these ends 48 and 50 on the one hand and 49 and 51 on the other hand, contact surfaces 52 and 53 are formed. As it is apparent in FIG. 12 thereto, in which a perspective representation of the cassette 6 with completely closed cover flaps 19 and 20 is shown, these contact surfaces 52 and 53 abut on each other on full surface.

Figure 12:
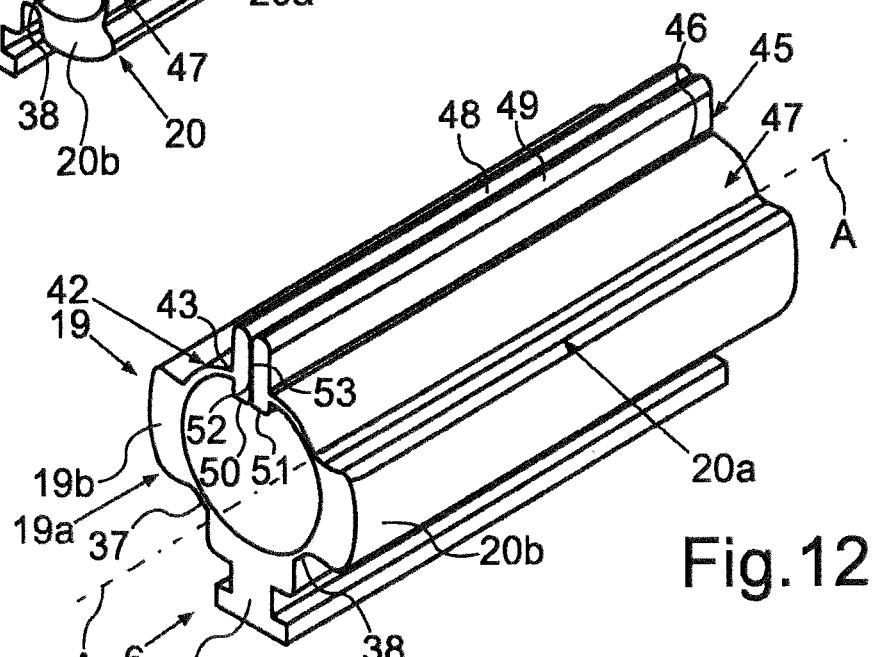
FIG. 12 is the cassette according to FIG. 11 with closed cover flaps.

In FIGS. 11 and 12, the tubular configuration of the cassette 6 is shown.

Figures 13A, 13B, 13C:
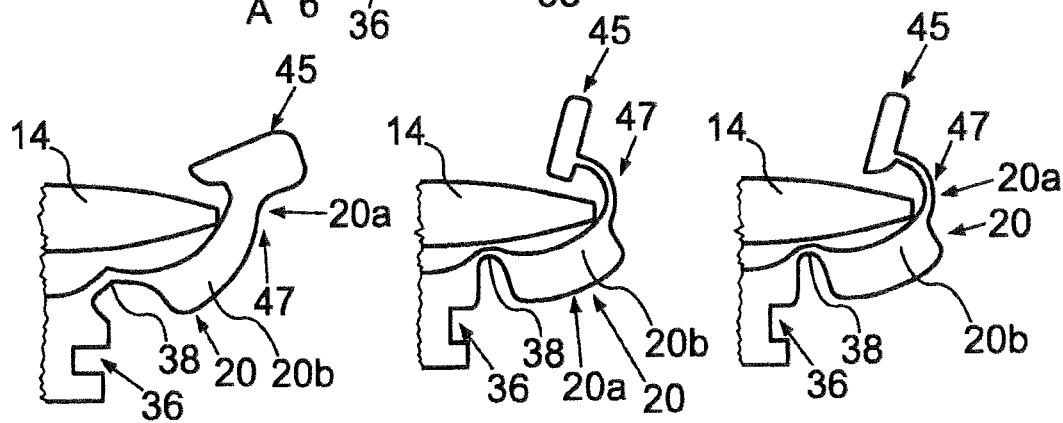
FIGS. 13A to 13C are sectional representations of partial views of various embodiments of cover flaps of the cassette according to FIG. 11 and FIG. 12 with partially shown intraocular lens.

In FIGS. 13A to 13C, front views are shown of the different configurations of a cassette 6 with introduced intraocular lens 14, wherein here differences in the cross-sectional configurations of the cover flaps 20 are in particular illustrated. In particular, different cross-sectional shapes of the hammerhead-like thickenings 44 and 45 are illustrated. Here, different configurations of those partial areas of the hammerhead shape result, which face the intraocular lens 14.

In the following FIG. 14 to FIG. 17, the scenario for pre-folding the intraocular lens 14 in the cassette 6 is explained in more detail.

Figure 14:
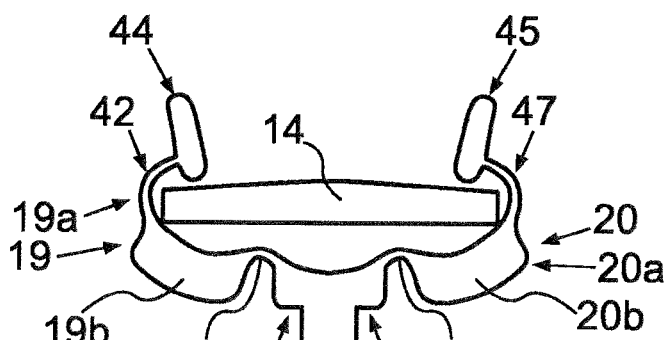
FIG. 14 is a sectional representation of the cassette according to FIGS. 11 and 12 with received intraocular lens in the opened state of the cover flaps.

For this purpose, in FIG. 14, the basic state is shown, in which the cover flaps 19 and 20 are completely opened and the cover flaps 19 and 20 are shown in themselves in a bent, but non-deformed basic state, wherein the basic shape of the arc-shaped flap sections 42 and 47 is therein shown. In this state, the intraocular lens 14 is not yet bent and rests on the inner sides of the cover flaps 19 and 20.

Figure 15:
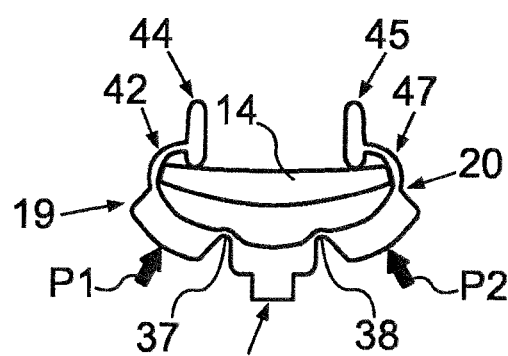
FIG. 15 is a sectional representation of the arrangement according to FIG. 14 in a first intermediate operating state with partially pivoted cover flaps.

Starting from this state, in an axial relative displacement to each other between the closing tips 15 and 16 and the cassette 6 then effected, contact of the guiding surfaces 27 of the closing tips 15 and 16 on the outer sides (19a, 20a) of the cover flaps 19 and 20 and they lift them according to the arrows P1 and P2 in FIG. 15 such that they are pivoted about the longitudinal axis A perpendicular to the figure plane.

Figure 16:
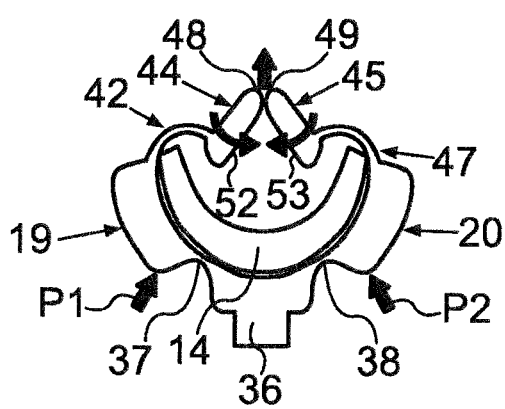
FIG. 16 is a sectional representation of the arrangement according to FIG. 14 and FIG. 15 with further pivoted cover flaps in a further intermediate operating state.

Since the flap sections 42 and 47 (second curved portions) have a smaller radius than the respective remainders (first curved portions) of the cover flaps 19 and 20, the thickenings 44 and 45 are guided inwards upon further pivoting about the longitudinal axis A such that they seat on the intraocular lens 14 and thus folding stabilizers are formed at least by the thickenings 44 and 45. At least from then, the intraocular lens 14 is clamped to a certain extent, and upon further axial relative displacement between the cassette 6 and the closing tips 15 and 16, further movement towards each other of the cover flaps 19 and 20 is effected such that the further intermediate position according to FIG. 16 is then reached. Therein, first, only the outer ends 48 and 49 contact each other. Mechanical contact is first only achieved at these ends (48, 49) and the contact surfaces 52 and 53 are incidentally still disposed without contact.

Figure 17:
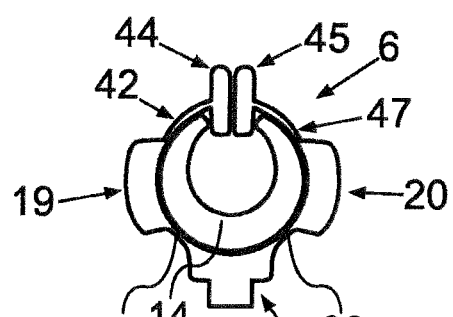
FIG. 17 is a sectional view of the arrangement according to FIG. 14 to FIG. 16 with closed cover flaps.

These deforming and folding sequences, as they are explained in FIG. 14 to FIG. 15 up to now, are an essential prerequisite for the desired defined pre-folding of the lens 14. By the specific shaping of the interior 11 of the support slide 10, then, it is further allowed that starting from the intermediate state in FIG. 16 the closed state of the cover flaps 19 and 20 can automatically appear. Due to the intrinsic deformation of the cover flaps 19 and 20, a certain tension state appears in the cover flaps 19 and 20. Due to the achieved abutment of the outer ends 48 and 49, in further movement of the cover flaps 19 and 20 towards each other, abutting of the contact surfaces 52 and 53 can be automatically achieved in the self-automatism, and the mutual support of the thickenings 44 and 45, outward movement, in particular outward snapping of these ends 44 and 45 can be achieved. Thereby, the inward bent basic state of the flap sections 42 and 47 is then automatically deformed and bent outwards, in particular snapping outwards is effected due to the supporting forces between the thickenings 44 and 45, and the self-stabilizing and self-retaining final state according to FIG. 17 is achieved. There, the contact surfaces 52 and 53 abut on each other on full surface, and a substantially symmetrical and round receiving space for the intraocular lens 14 is formed viewed in cross-section, which is only interrupted by the hammerhead-like thickenings 44 and 45. At least from the state according to FIG. 16, the ceiling side 41 is provided with a free space formed correspondingly to the top, such that upward snapping of the thickenings 44 and 45 is then allowed. This is shown in the sectional representation according to FIG. 18, in which the final state of the cassette 6 with the intraocular lens 14, as is shown in FIG. 17, is shown in the state disposed in the injector device 1 and thus also the device 9.

Figure 18:
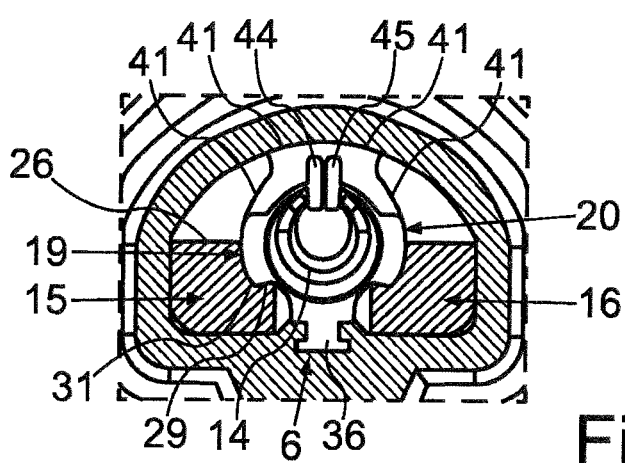
FIG. 18 is a sectional representation of the injector device according to FIGS. 1 to 3 with the cassette with closed cover flaps according to the representation in FIG. 17.

As is apparent in FIG. 18, the shaping of the outer side (19a, 20a) of the cover flaps 19 and 20 is preferably such that large-area, in particular full-area and relatively exactly fitting abutment on guiding surfaces 27 of the closing tips 15 and 16 is formed at least in this final position.

Figure 19:
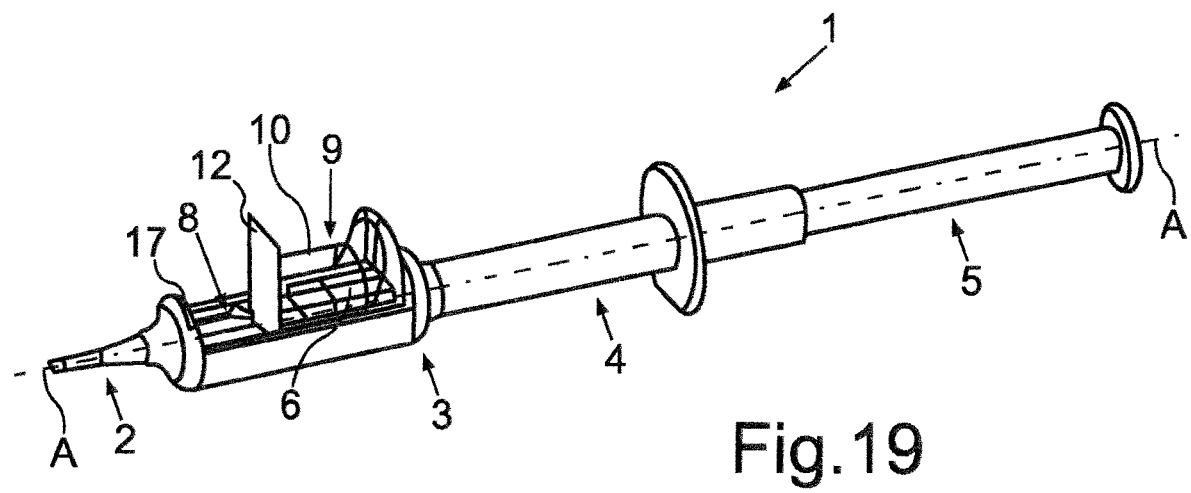
FIG. 19 is a perspective representation of a further embodiment of an injector device according to the invention.

In FIG. 19, in a perspective representation, a further embodiment of an injector device 1 is shown. Unlike the representation in the previous embodiment, here, it is provided that the injector tube 3 is integrally formed with the piston tube 4. This means that the two tubes 3 and 4 are fixedly connected to each other, in particular integrally formed.

Here too, the upward open receiving space 8 is formed and the device 9 with a cassette 6 and a support slide 10 is inserted.

Figure 20:
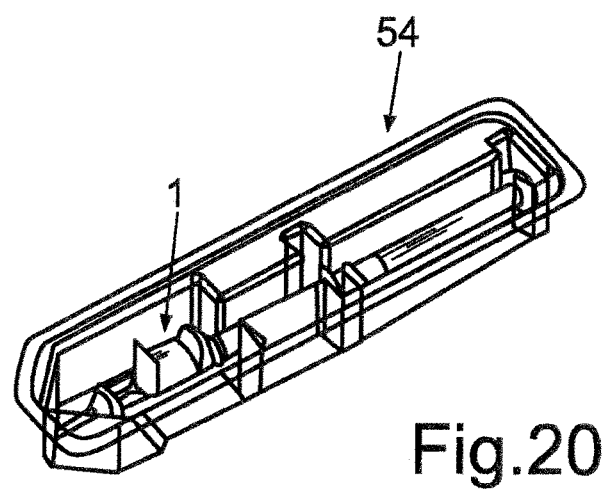
FIG. 20 is a perspective representation of a packaging and transport device with an injector device according to FIG. 19.

In FIG. 20, an embodiment of a packaging and transport device 54 is shown. The container in this respect is formed for receiving the injector device 1, as it was explained in FIGS. 1 to 4, or for receiving the injector device 1 according to FIG. 19. It is filled with a corresponding sterile liquid, wherein a corresponding sterile liquid is already provided in the cassette 6 for flushing around the lens 14 here too. The container is then closed by a covering, as for example a foil, in sterile manner and can then be delivered from the manufacturer to the medical personnel in this compact configuration. The medical personnel then only has to remove the completely loaded injector or injector device 1 from the device 54 and perform no further loading of the injector device 1 with a cassette at all or optionally the removal of an intraocular lens 14 from a further separately delivered container. Thereby, the handling is substantially simplified and errors in loading can be avoided.

In FIG. 21, a plan view of the injector tube 3 with the injector tip 2 is shown, wherein only the front area with the receiving space 8 and removed device 9 is illustrated. In a bottom 55 of the injector tube 3, the guiding track or the guiding slit 32 is apparent. The closing tips 15 and 16 are illustrated and the spaced arrangement and connection to the bounding wall 17 with front ends 56 and 57 is shown.

In this configuration, unlike the embodiment explained heretofore, it is provided that a rear section 22 extending up to the dashed line, forms in tapering manner. This rear section 22 includes a rear guiding surface section 58 of the guiding surface 27, which is formed in the manner of a steep turn. This means that it does not extend in a plane, but is formed curved and tortuous in the space. This steep turn-like guiding surface section 58 extends from a rear end 23 of the closing tip 15 up to a front end 49. Thus, it extends over the entire length of the rear section 22 of the closing tip 15. Moreover, this guiding surface section 58 is configured such that a rear area end 60 is thinner or narrower than the middle piece 61 such that this area section 58 continuously expands and increases starting from this rear end 60 and then again tapers starting from the maximum width up to the front end 59. Thus, a type of boomerang shape is virtually formed, which moreover also forms a certain winding in the manner of a helical section. Here too, the explanation to the closing tip 15 applies to the closing tip 16 in analogous manner since it is identically formed and a symmetrical configuration to the longitudinal axis A is generated.

Adjoining to the rear length section 22 of the closing tip 15, the front length section 25 is formed. It includes a flat top side 26, which adjoins to the front first section 22 at an upper edge 62 of the steep turn-like guiding surface section 58.

The guiding surface 27 has a front guiding surface section 63 besides the steep turn-like guiding surface section 58, which extends parallel to the longitudinal axis A. As is apparent from the representation in FIG. 21, a radial distance and thus a distance perpendicular to the longitudinal axis A between the rear ends 60 of the tips 15 and 16 is larger than a corresponding distance between the front ends 59 of the front guiding surface section 63, wherein this smaller distance then achieved on the front ends 59 corresponds to equal to the distance between the front guiding surface sections 63, which in particular then remains constant over the entire length of the front guiding surface sections 63.

By these guiding surface sections 63 and the spacing thereof, a guiding slit 64 is formed. The substantially closed cover flaps 19 and 20 of the cassette 6 are guided in it and retained in their position until the cassette 6 has assumed the final position achieved for the axial displacement direction.

In FIG. 22, a perspective representation of FIG. 21 is shown.

In FIG. 23, a side view is shown, in which only the injector tip 2 and the closing tip 16 are shown. In this respect, the contour of the outer edge of the guiding surface 27 is illustrated in the area of the guiding surface section 58. An outer side 65 adjoining to the top side and the guiding surface section 58 is also illustrated.

In FIG. 24, a plan view of the components in FIG. 23 is shown, wherein reference is made to the explanations to FIGS. 21 to 23 with respect to the features and configurations.

Figure 25:
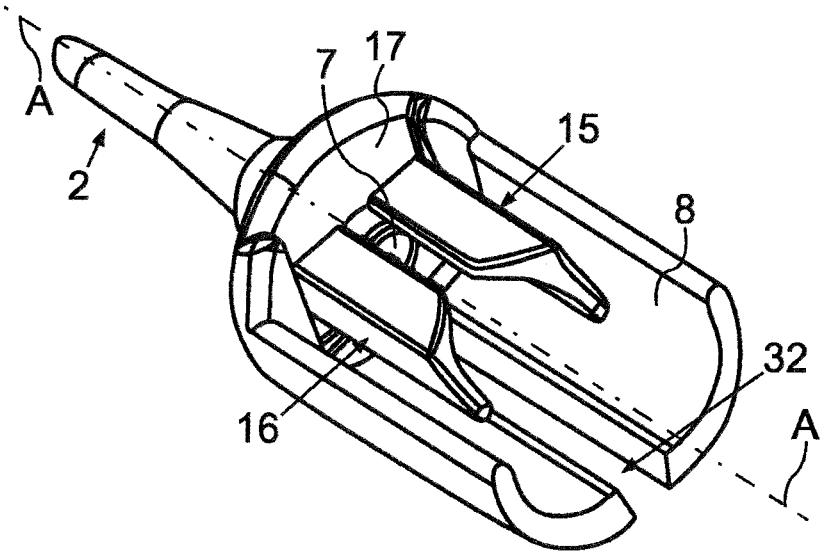
FIG. 25 is a further perspective representation of the components according to FIGS. 21 and 22.

In FIG. 25, a further perspective representation of the implementations in FIGS. 21 to 24 is shown.

The position of the closing tips 15 and 16 relative to the guide channel 7 is shown.

Figure 26:
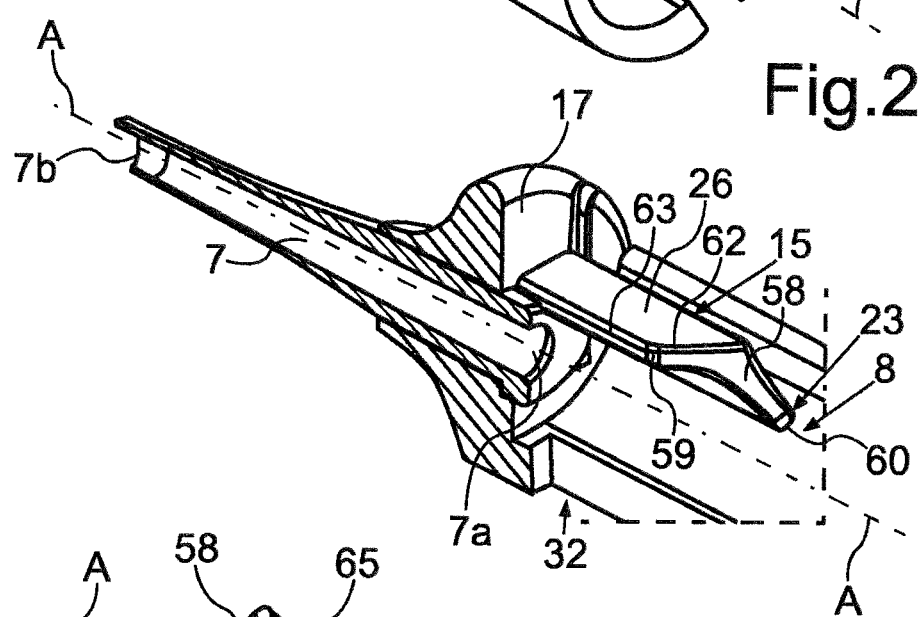
FIG. 26 is a perspective sectional view of the representation in FIG. 25.

A more accurate view is apparent in the sectional representation in FIG. 26 thereto, wherein the sectional plane here includes the longitudinal axis A.

Figure 27:
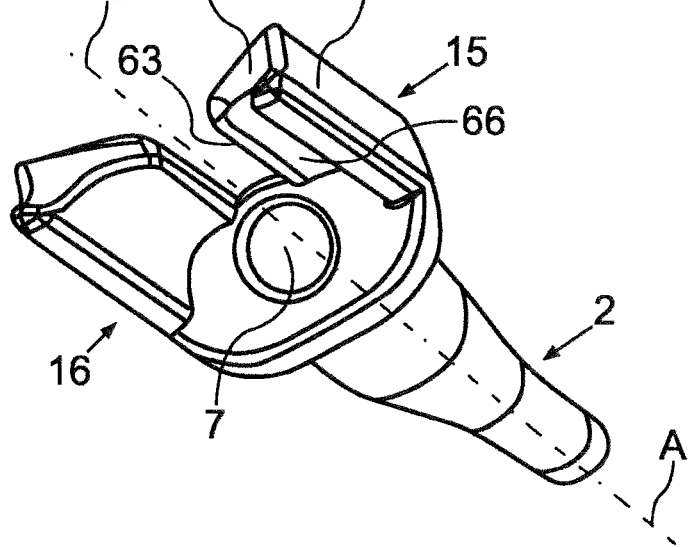
FIG. 27 is a perspective representation of the components as they are shown in FIGS. 23 and 24.

Moreover, in FIGS. 25 to 27, the shape and curvature of the guiding surface section 58 in the three-dimensional space is apparent in even more detailed manner. The crescent or boomerang-like area shape with the additional uneven winding for configuring a steep turn-like shaping is shown.

Moreover, the curved or dome-like shape of a bottom side 66 adjoining to the outer side 65 and the top side 26 as well as the section 58 is also shown. The bottom side 66 transitions into the front guiding surface section 63, which then joins to the top side 26. By these mentioned area parts, a closing tip 15 and 16 is formed, respectively.

In FIG. 28, a perspective representation of the embodiment of a device 9 having a cassette 6 and a support slide 10 is shown.

In FIG. 29, a perspective view is illustrated thereto, wherein the front-side covering in the form of the covering element 12 is already removed.

In this implementation, the support slide 10 includes an upward protruding plate-like handle part 67, which a user can grip to be able to displace the device 9 in the direction of the longitudinal axis A relative to the closing tips 15 and 16 in the receiving space 8.

In the representation according to FIG. 29, the multiple guiding elements in the form of blades or locking elements 39 are illustrated, which are attached to the bottom 40.

In this embodiment, the cassette 6 is additionally formed with a securing cover 68 besides the base part 36 and the two wing-like cover flaps 19 and 20. The securing cover 68 is preferably also integrally formed with the other components of the cassette 6. Such a securing cover 68 can also be provided in the other implementations of cassettes 6 explained heretofore.

The securing cover 68 is attached to the base part 36 pivotable relative thereto, wherein in particular a connection via a film hinge 72 (FIG. 33) is provided thereto.

In the opened state of the cover flaps 19 and 20, the securing cover 68 is closed. It has a hook-shaped securing bracket 69 at its front end such that the intraocular lens 14 cannot fall or slip out of the cassette 6 neither to the top nor to the front.

In FIG. 30, a further perspective representation of the device 9 is shown in the state inserted into the receiving space 8. The locked arrangement is apparent, wherein the guide blades 39 are disposed in the guiding slit 32 thereto and extend through it such that engaging behind the outer side of the injector tube 3 is effected with the guide blades 39. Thereby, the axial displacement is simplest possible and yet slipping or canting in another spatial direction is prevented. By the flexibility of the guide blades 39, simple insertion and locking of the device 9 in the receiving space 8 and the guiding slit 32 can be effected.

In FIG. 31, a front view of the representation in FIG. 30 is shown. In this respect, the position of the cassette 6 in the interior 11 is apparent.

Figure 32:
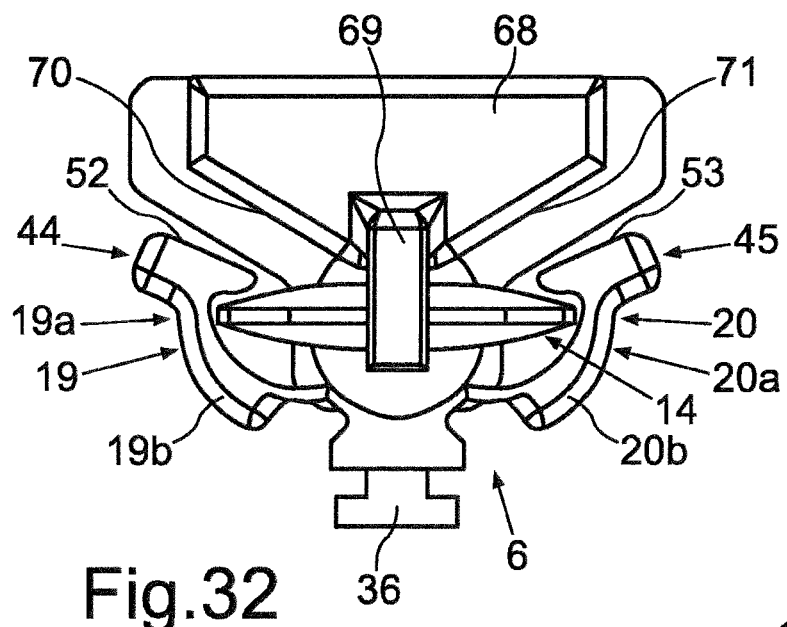
FIG. 32 is a front view of an embodiment of a cassette according to the invention for receiving an intraocular lens.

In FIG. 32, a view from the front to the cassette 6, as it was explained in FIGS. 28 to 31, is shown. The intraocular lens 14 is disposed therein in the base position.

Starting from the representation in FIG. 32, the securing cover 68 can be automatically lifted and opened. Thereto, according to the representation in FIG. 33, pivoting of the cover flaps 19 and 20 around the longitudinal axis A is effected, wherein this is effected by the already explained scenarios with the closing tips 15 and 16.

Figure 33:
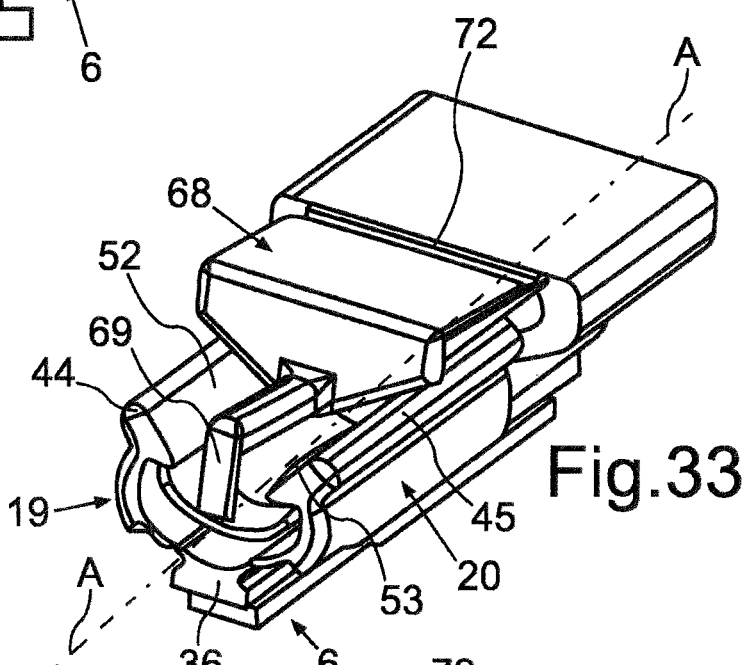
FIG. 33 is a perspective representation of the cassette according to FIG. 32 with partially lifted pivoting cover and partially closed cover flaps.

During this pivoting of the cover flaps 19 and 20, contact of the thickenings 44 and 45 with the securing cover 68 is then achieved. Thereto, it includes oblique lifting elements, in particular lifting flanks 70 and 71. With further closing of the cover flaps 19 and 20, the thickenings 44 and 45 slide along these oblique lifting flanks 70 and 71, whereby the securing cover 68 is lifted, as it is illustrated in FIG. 33. Therein, the film hinge 72 is horizontally oriented such that the cover 68 is upward lifted pivotable around this axis as it is illustrated by the arrows.

Figure 34:
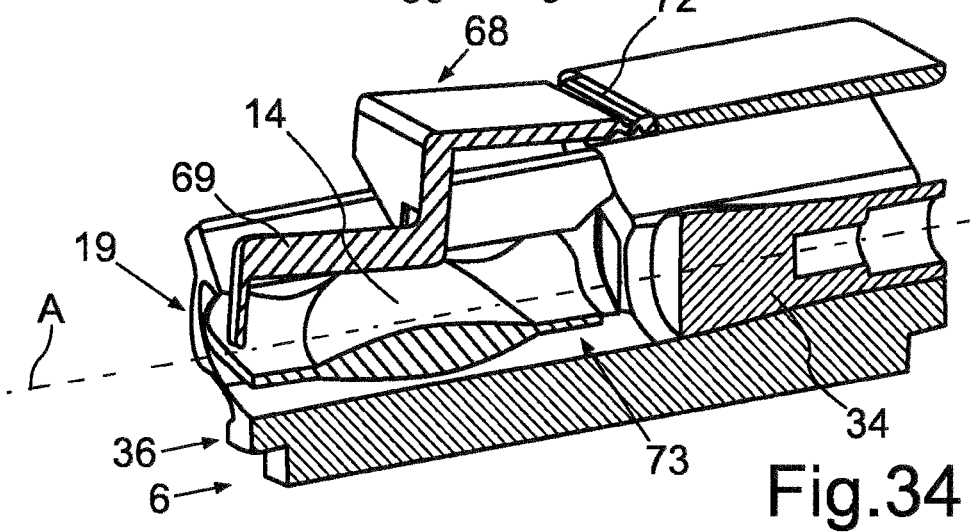
FIG. 34 is a sectional representation of the implementation in FIG. 33.

In FIG. 34, a sectional representation of the perspective view in FIG. 33 is shown. Therein, the intraocular lens 14 is disposed in an interior 73, which is bounded by the cover flaps 19 and 20 and the base part 36 in the closed state of the cover flaps 19 and 20.

Figure 35:
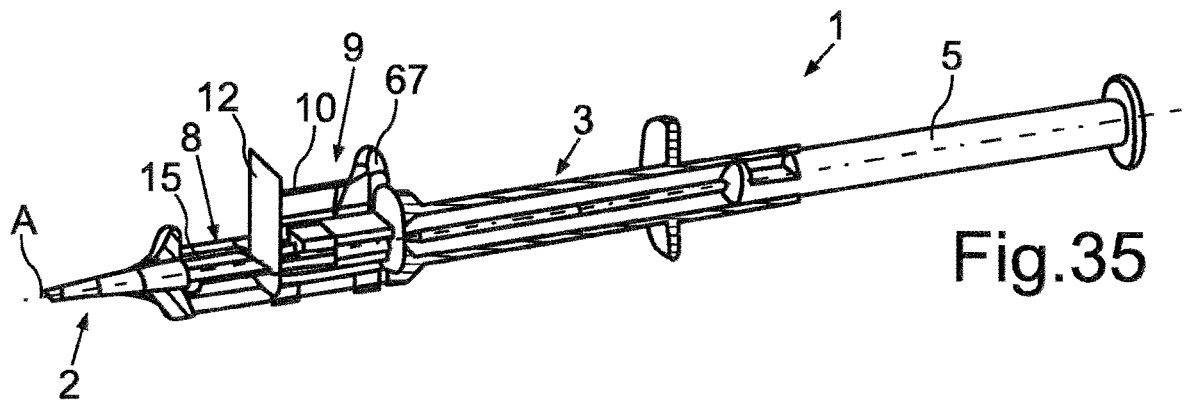
FIG. 35 is a sectional representation of the injector device according to FIG. 19 in a first operating state.

In FIG. 35, a perspective representation of the injector device 1 in an operating state is shown, in which the device 9 is disposed in the receiving space 8 in a rear base position.

Figure 36:
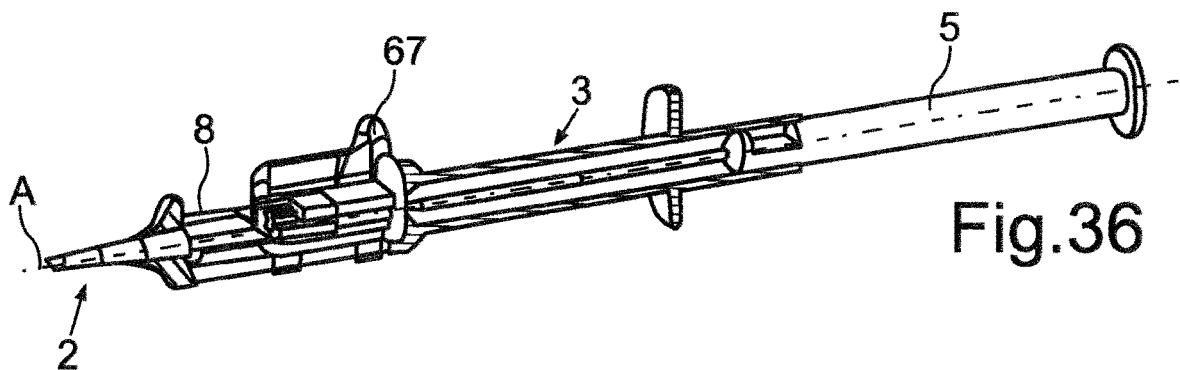
FIG. 36 is a sectional representation of the injector device according to FIG. 35 in a second operating state.
Figure 37:
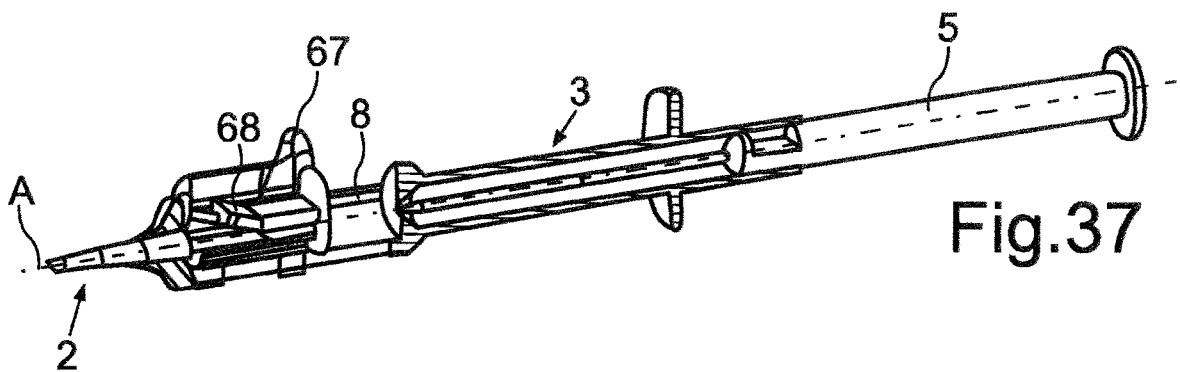
FIG. 37 is a sectional representation of the injector device according to FIG. 35 and FIG. 36 in a further operating state.

Starting from this state, in the following, the front-side covering in the form of the covering element 12 is then removed by a user, as it is shown in FIG. 36. In the following, the device 9 with the support slide 10 and the cassette 6 is then axially forward shifted towards the injector tip 2 until it has reached the front final position according to the representation in FIG. 37. During this shifting operation between the positions in FIG. 36 and FIG. 37, the automatic closure of the cassette 6 is achieved since the closing tips 15 and 16 engage with the interior 11 of the support slide 10 and lift and close the cover flaps 19 and 20. Therein, the intraocular lens 14 in the cassette 6 is brought in a pre-folded state. As is apparent in FIG. 37, the securing cover 68 is then also automatically lifted.

Figure 38:
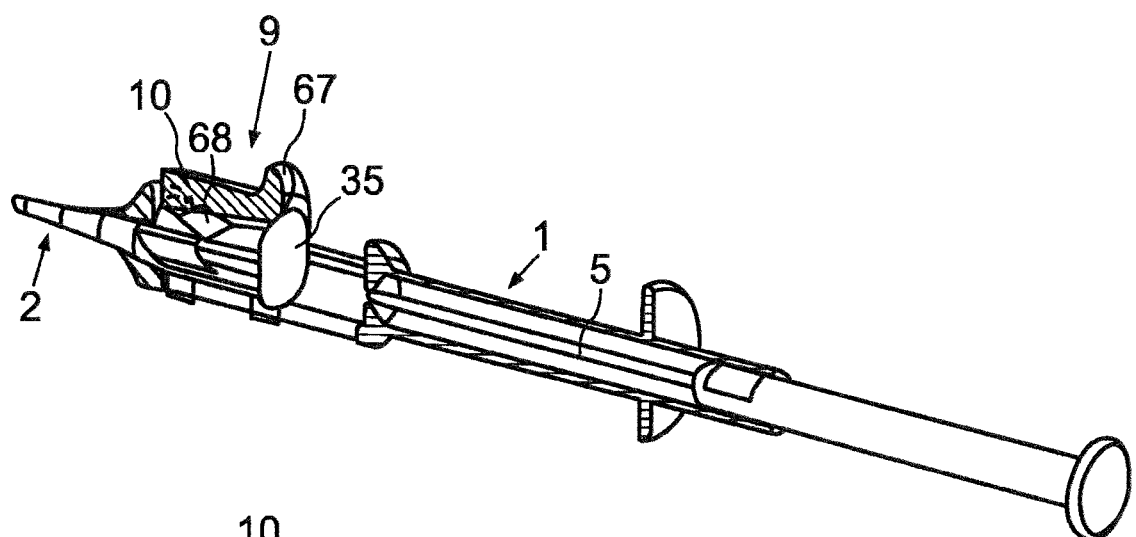
FIG. 38 is a perspective representation of the injector device according to FIG. 35 to FIG. 37 in a further operating state.
Figure 39:
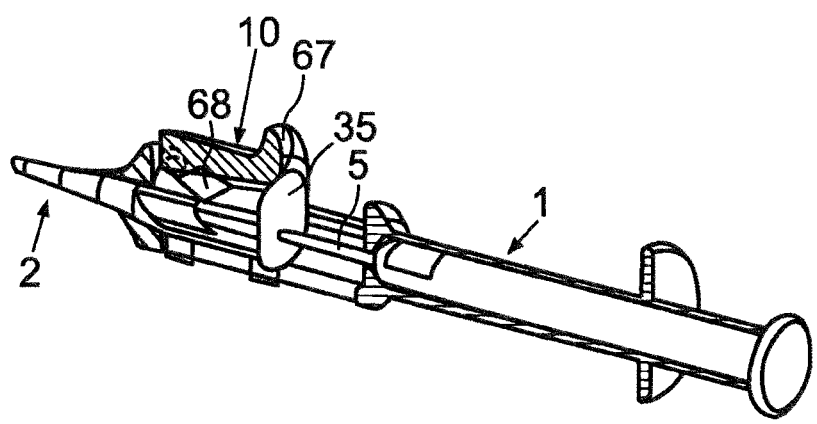
FIG. 39 is a perspective sectional representation of the injector device according to FIG. 35 to FIG. 38 in a further operating state.
Figure 40:
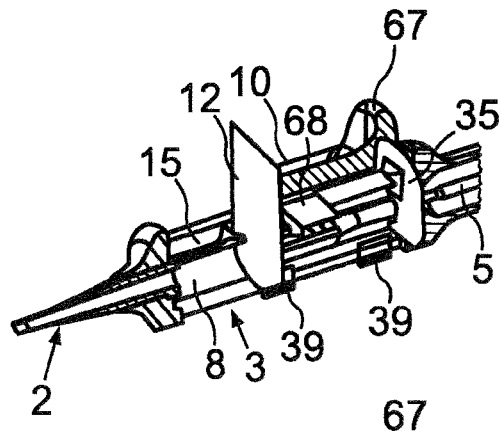
FIG. 40 is a representation of a partial section of the injector device according to FIG. 35.
Figure 41:
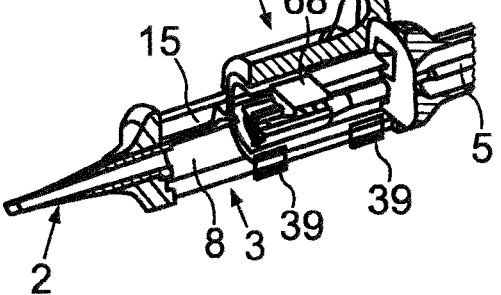
FIG. 41 is an enlarged partial representation of the injector device according to FIG. 36.
Figure 42:
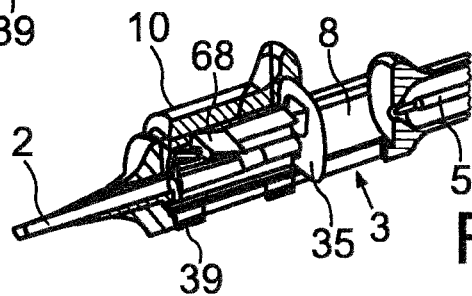
FIG. 42 is an enlarged representation of the injector device according to FIG. 37.
Figure 43:
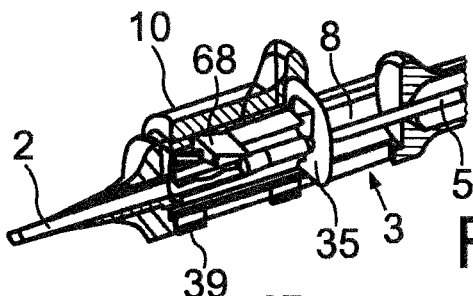
FIG. 43 is an enlarged representation of a partial section of the injector device according to FIG. 38.
Figure 44:
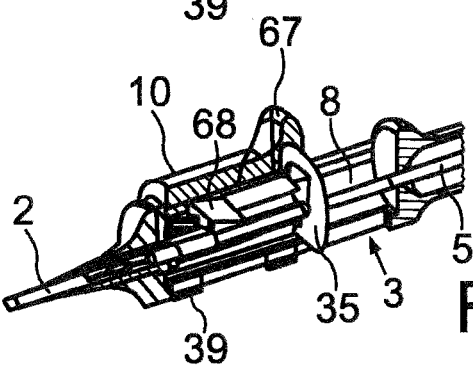
FIG. 44 is an enlarged partial representation of the injector device according to FIG. 39.

In a further step, according to the representation in FIG. 38, the piston 5 is then forward shifted until it contacts the rear cover element 35. It is in particular formed such that it can be pierced by the piston 5, as it is shown in FIG. 39. Then, the elastic shift-out element 34 is shifted forward by the piston 5 and the intraocular lens 14 is contacted and then shifted out of the cassette 6 into the guide channel 7. There, it is further folded since the guide channel 7 tapers up to the outlet 7b. In a then maximally folded position, the intraocular lens 14 is then shifted out of the injector tip 2 and shifted into the eye.

In FIGS. 40 to 44, the operating states explained based on FIGS. 35 to 39 are again illustrated, wherein only the area of the injector device 1 is respectively shown, which is formed forward from the receiving space 8.

Figure 45:
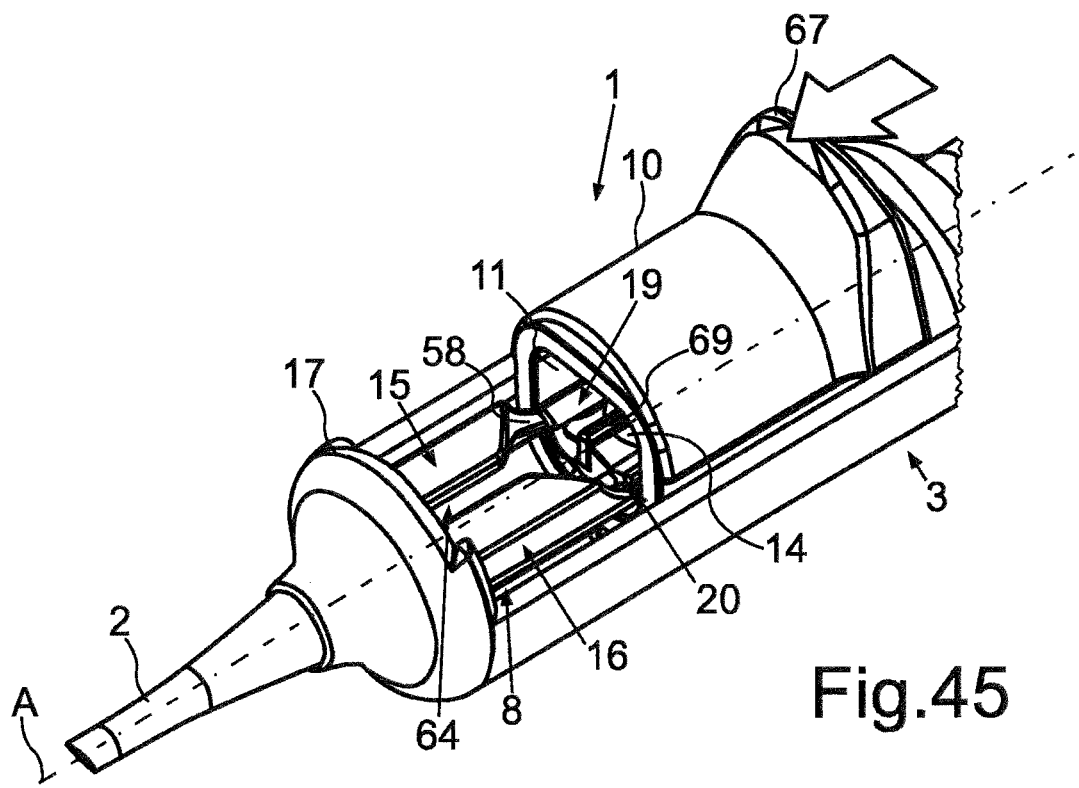
FIG. 45 is an enlarged representation of a partial section of the injector device according to FIGS. 35 to 39 in a further intermediate operating state between the operating states according to FIGS. 36 and 37; and, FIG. 46 is an enlarged representation of the view in FIG. 45.

In FIG. 45, a further perspective representation of partial components of the injector device 1 is shown, wherein a state is shown here, in which the closing tips 15 and 16 extend linearly into the interior 11 and the cover flaps 19 and 20 just contact on the outer sides (19a, 20a) to then pivot around the axis A afterwards and bring into the closure position.

Figure 46:
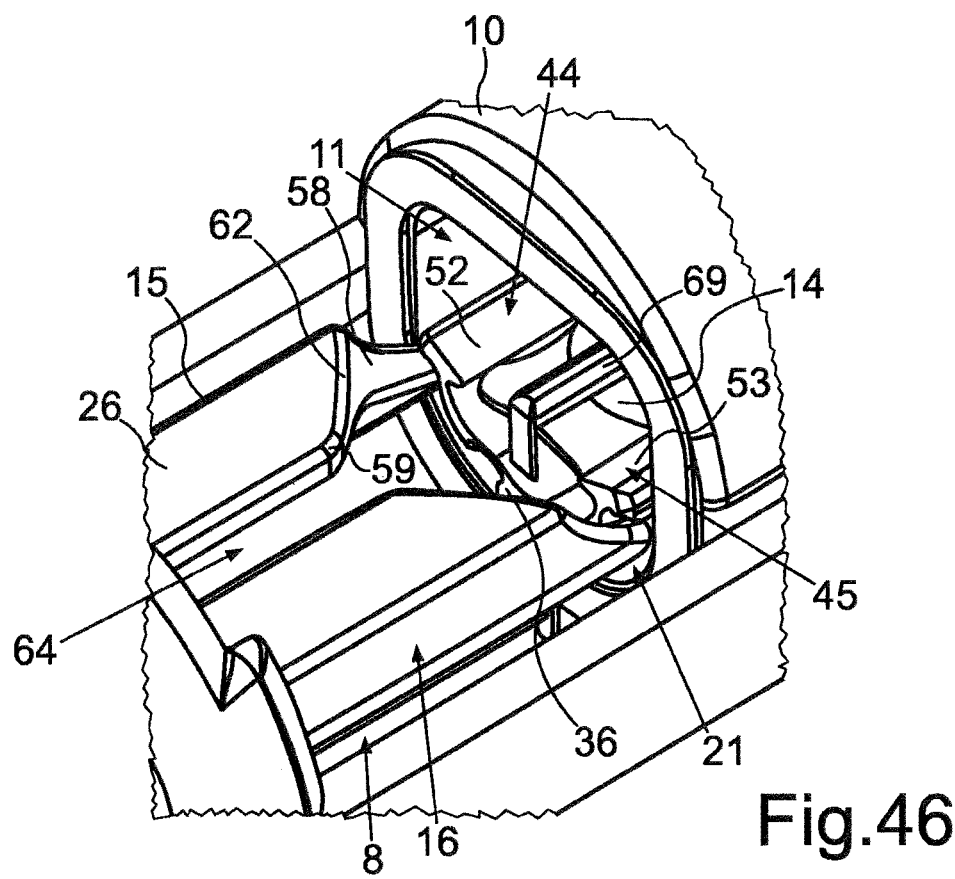

Thereto, a further enlarged section of the representation in FIG. 45 is shown in FIG. 46. In particular, the engagement of the closing tips 15 and 16 with the outer sides 19a, 20a of the cover flaps 19 and 20, in particular and preferably on the outer sides of the thickenings 44 and 45, is shown here too. By the specific shaping of the closing tips 15 and 16, in particular the guiding surfaces 27, which is adapted to the shaping of the outer side of the cover flaps 19 and 20, optimum pivoting operation of the cover flaps 19 and 20 without laterally slipping past can be achieved.

It is understood that the foregoing description is that of the preferred embodiments of the invention and that various changes and modifications may be made thereto without departing from the spirit and scope of the invention as defined in the appended claims.

What is claimed is:

1. A cassette for receiving and accommodating an intraocular lens therein, the lens having top and bottom broad sides and a peripheral edge extending between said broad sides, the cassette defining a longitudinal axis (A) and comprising:
   a base part;
   pivotable cover flaps arranged on said base part so as to be pivotable about said longitudinal axis (A) from a base position to a closed position in response to a lateral force applied thereagainst and so enclose a space therebetween for said intraocular lens;
   said cover flaps being bendable so as to deform in a defined manner as they move from said base position into said closed position;
   each of said cover flaps having a first curved portion having a first radius of curvature and being pivotably connected to said base part and a second curved portion extending directly from said first curved portion;
   each of said second curved portions having a free end and a T-shaped thickening at said free end when viewed in a section view lying in a plane perpendicular to said longitudinal axis (A);
   said first and second curved portions of each of said cover flaps having a concave curvature facing toward said longitudinal axis; and,
   said second curved portions having a second radius of curvature smaller than said first radius of curvature to guide said T-shaped thickenings inwardly in response to pivoting of said cover flaps to seat directly on one of said broad sides of said intraocular lens at respective locations thereon spaced away from said peripheral edge thereof as a folding stabilizer during the movement of said cover flaps toward said closed position whereat said T-shaped thickenings mutually abut to provide a mechanically self-stabilizing annular structure closed in cross-section and said cover flaps conjointly delimiting said space and directly enclosing said intraocular lens.

2. The cassette of claim 1, wherein said T-shaped thickenings have respective outer ends which mutually contact when said cover flaps are moved toward said closed position and, with a further closing of said cover flaps toward each other, said second curved portions are deformable with a further closing and mutual contact engagement of said thickenings.

3. The cassette of claim 1, wherein said cassette is mountable in an injection device having a longitudinal axis corresponding to said longitudinal axis (A) of said cassette and wherein said injection device includes closure tips; and, wherein said cassette is comprised in that:
   said T-shaped thickenings have respective outer ends which mutually contact when said cover flaps are moved toward said closed position and, with a further closing of said cover flaps toward each other, said second curved portions are deformable with the further closing and mutual contact engagement of said thickenings; and,
   said cover flaps have respective outer sides whereat respective risers are disposed and configured for a guiding engagement of said closure tips for automatically closing said cover flaps.

4. The cassette of claim 3, wherein, when viewed in section, each one of said second curved portions is formed between the riser and the T-shaped thickening corresponding thereto with said second curved portion being thinner up to said free end thereof when compared to the thickening and the riser and said second curved portion is bendable in a defined manner upon the closing of said cover flaps.

5. An injector device for introducing an intraocular lens into an eye, the injector device defining a longitudinal axis and comprising:
   an injector tip defining a through guide channel for the intraocular lens;
   said guide channel having a rear inlet and a front outlet;
   a receiving space extending rearwardly from said rear inlet;
   closure tips extending rearwardly from said rear inlet toward said receiving space;
   a cassette for accommodating the intraocular lens therein and said cassette being mounted in said receiving space;
   said cassette defining a longitudinal axis (A) and including:
   a base part;
   pivotable cover flaps arranged on said base part so as to be pivotable about said longitudinal axis (A) from a base position to a closed position; and,
   said cover flaps being curved at least in selected regions thereof and being configured to be bendable so as to deform in a defined manner when said cover flaps are moved from said base position to said closed position in response to a mutual contact engagement between said cover flaps and said closure tips during a relative movement therebetween along said longitudinal axis (A).

6. The injector device of claim 5, wherein said cover flaps have respective arc-shaped flap sections and said cover flaps are curved in said base position thereof.

7. The injector device of claim 6, wherein said flap sections are configured to be arc-shaped at least in selected regions about said longitudinal axis (A) which are intrinsically reversibly bendable in a direction perpendicular to said longitudinal axis (A).

8. The injector device of claim 7, wherein each of said cover flaps has a free end and a T-shaped thickening at said free end when viewed in a section view lying in a plane perpendicular to said longitudinal axis (A).

9. The injector device of claim 8, wherein each of the T-shaped thickenings are so formed that they are at least temporarily seated on said intraocular lens as a fold stabilizer when said cover flaps are pivoted and bent into said closed position.

10. The injector device of claim 9, wherein said T-shaped thickenings have respective outer ends which mutually contact when said cover flaps are moved toward said closed position and, with a further closing of said cover flaps toward each other, said flap sections are deformable with a further closing and mutual contact engagement of said thickenings.

11. The injector device of claim 10, said cover flaps having respective outer sides whereat respective risers are disposed and configured for a guiding engagement of said closure tips for automatically closing said cover flaps.

12. The injector device of claim 11, wherein, when viewed in section, each one of said flap sections is formed between the riser and the T-shaped thickening corresponding thereto with said one flap section being thinner when compared to the thickening and the riser and said one flap section is bendable in a defined manner upon the closing of said cover flaps.

13. The injector device of claim 5, wherein said cassette further comprises:
an upwardly pivotable securing cover for the intraocular lens;
said securing cover being pivotally connected to said base part so as to be pivotally liftable from a closed state wherein said cover flaps are in said base position thereof to an open state in response to a movement of said cover flaps to said closed position thereof; and,
said securing cover having respective lifting flanks against which said cover flaps come into contact engagement to move said securing cover into said open state thereof.

14. The injector device of claim 13, wherein said securing cover has a hook-shaped securing bracket extending forward in the direction of said longitudinal axis (A).

15. The injector device of claim 13, said securing cover and said base part conjointly defining an interface; and, said cassette further comprising a film hinge at said interface connecting said securing cover to said base part so as to permit said securing cover to be pivoted upwardly and downwardly.

16. A cassette for accommodating an intraocular lens, the cassette defining a longitudinal axis (A) and comprising:
a base part;
pivotable cover flaps arranged on said base part so as to be pivotable about said longitudinal axis (A) from a base position to a closed position;
said cover flaps being curved at least in selected regions thereof and being configured to be bendable so as to deform in a defined manner when said cover flaps are moved from said base position to said closed position;
an upwardly pivotable securing cover for the intraocular lens;
said securing cover being pivotally connected to said base part so as to be pivotally liftable from a closed state wherein said cover flaps are in said base position thereof to an open state in response to a movement of said cover flaps to said closed position thereof; and,
said securing cover having respective lifting flanks against which said cover flaps come into contact engagement to move said securing cover into said open state thereof.

17. The cassette of claim 16, wherein said securing cover has a hook-shaped securing bracket extending forward in the direction of said longitudinal axis (A).

18. The cassette of claim 16, said securing cover and said base part conjointly defining an interface; and, said cassette further comprising a film hinge at said interface connecting said securing cover to said base part so as to permit said securing cover to be pivoted upwardly and downwardly.

19. An injector device for introducing an intraocular lens into an eye, the injector device defining a longitudinal axis and comprising:
an injector tip defining a through guide channel for the intraocular lens;
said guide channel having a rear inlet and a front outlet;
a receiving space extending rearwardly from said rear inlet;
closure tips;
a cassette for accommodating the intraocular lens and said cassette being mounted in said receiving space;
said cassette defining a longitudinal axis (A) and including:
a base part;
pivotable cover flaps arranged on said base part so as to be pivotable about said longitudinal axis (A) from a base position to a closed position;
said cover flaps being curved at least in selected regions thereof and being configured to be bendable so as to deform in a defined manner when said cover flaps are moved from said base position to said closed position; and,
said cover flaps have respective outer sides whereat respective risers are disposed and configured to permit a guiding engagement of said closure tips for automatically closing said cover flaps in response to a mutual contact engagement between said risers and said closure tips during a relative movement therebetween along said longitudinal axis (A).

20. An injector device for introducing an intraocular lens into an eye, the injector device defining a longitudinal axis and comprising:
an injector tip defining a through guide channel for the intraocular lens;
said guide channel having a rear inlet and a front outlet;
a receiving space extending rearwardly from said rear inlet;
closure tips extending along said longitudinal axis away from said rear inlet toward said receiving space;
a cassette for holding the intraocular lens;

a support slide accommodating said cassette therein and said support slide being disposed in said receiving space;

said cassette defining a longitudinal axis (A) corresponding to said longitudinal axis of said injector device;

said cassette including:

a base part;

pivotable cover flaps arranged on said base part so as to be pivotable about said longitudinal axis (A) from a base position to a closed position;

said cover flaps being curved at least in selected regions thereof and being configured to be bendable so as to deform in a defined manner when said cover flaps are moved from said base position to said closed position; and, said cover flaps have respective outer sides whereat said closure tips come into contact engagement with corresponding ones of said outer sides in response to a movement of said support slide with said cassette along said longitudinal axis (A) to close said cover flaps to fold said lens in preparation for insertion into said injector tip.

21. The injector device of claim 20, wherein said closure tips are mutually parallel and arranged spaced from each other.

22. The injector device of claim 20, wherein said support slide is formed as an integral tubular member defining an inner curved wall surface having a first radius of curvature; said cover flaps have outer ends which trace a curved path as they are pivoted from said base position to said closed position; and, said curved path defines a second radius of curvature less than said first radius of curvature thereby facilitating an unimpeded movement of said cover flaps as they move to said closed position.

23. A cassette for receiving and accommodating an intraocular lens therein, the lens having top and bottom broad sides and a peripheral edge extending between said broad sides, the cassette defining a longitudinal axis (A) and comprising:

a base part;

pivotable cover flaps arranged on said base part so as to be pivotable about said longitudinal axis (A) from a base position to a closed position in response to a lateral force applied thereagainst and so enclose a space therebetween for said intraocular lens;

said cover flaps being bendable so as to deform in a defined manner as they move from said base position into said closed position;

each of said cover flaps having a first curved portion having a first radius of curvature and being pivotably connected to said base part and a second curved portion extending directly from said first curved portion;

each of said second curved portions having a free end and a T-shaped thickening at said free end when viewed in a section view lying in a plane perpendicular to said longitudinal axis (A);

said first and second curved portions of each of said cover flaps having a concave curvature facing toward said longitudinal axis;

said second curved portions having a second radius of curvature smaller than said first radius of curvature to guide said T-shaped thickenings inwardly in response to pivoting of said cover flaps to seat directly on one of said broad sides of said intraocular lens at respective locations thereon spaced away from said peripheral edge thereof as a folding stabilizer during the movement of said cover flaps toward said closed position;

said T-shaped thickenings having respective end surfaces which are in mutual abutting engagement when said cover flaps are in said closed position and so conjointly define a contact interface and provide a mechanically self-stabilizing annular structure closed in cross-section and said cover flaps conjointly delimiting said space and directly enclosing said intraocular lens; and, said T-shaped thickenings each having a portion thereof extending into said space along said contact interface to receive respective diametrically opposite edge portions of said peripheral edge of said intraocular lens thereon preventing a mutual contact of said respective diametrically opposite edge portions when said cover flaps are in said closed position.

24. A cassette assembly for insertion into a receptacle of an injector device for introducing an intraocular lens into an eye, the lens having top and bottom broad sides and a peripheral edge extending between said broad sides, the cassette assembly comprising:

a support slide formed as an annular component having an inner wall delimiting an interior;

a cassette accommodating the intraocular lens and defining a longitudinal axis (A);

said cassette being disposed in said interior and including:

a base part;

pivotable cover flaps arranged on said base part so as to be pivotable about said longitudinal axis (A) from a base position to a closed position in response to a lateral force applied thereagainst and so conjointly form an annular wall enclosing a space therebetween for said intraocular lens;

said cover flaps being bendable within said interior so as to deform in a defined manner as they move from said base position into said closed position;

each of said cover flaps having a first curved portion having a first radius of curvature and being pivotably connected to said base part and a second curved portion extending directly from said first curved portion;

said first and second curved portions of each of said cover flaps having a concave curvature facing toward said longitudinal axis;

each of said second curved portions having a free end and a T-shaped thickening at said free end when viewed in a section view lying in a plane perpendicular to said longitudinal axis (A);

said second curved portions having a second radius of curvature smaller than said first radius of curvature to guide said T-shaped thickenings inwardly in response to pivoting of said cover flaps to seat directly on one of said broad sides of said intraocular lens during the movement of said cover flaps toward said closed position whereat said T-shaped thickenings mutually abut to provide a mechanically self-stabilizing structure closed in cross-section and directly including the intraocular lens; and, said inner wall of said support slide being shaped to have a curvature to allow an unimpeded movement of said cover flaps during said movement of said cover flaps in said interior from said base position to said closed position.

25. The cassette assembly of claim 24, wherein said inner wall has a radius of curvature larger than the radii of curvature of said cover flaps.

26. A cassette assembly for insertion into a receptacle of an injector device for introducing an intraocular lens into an eye, the lens having top and bottom broad sides and a peripheral edge extending between said broad sides, the cassette assembly comprising:

a support slide formed as an annular component having an inner wall delimiting an interior;

a cassette accommodating the intraocular lens and defining a longitudinal axis (A);

said cassette being disposed in said interior and including:

a base part;

pivotable cover flaps arranged on said base part so as to be pivotable about said longitudinal axis (A) from a base position to a closed position in response to a lateral force applied thereagainst and so enclose a space therebetween for said intraocular lens;

said cover flaps being bendable within said interior so as to deform in a defined manner as they move from said base position into said closed position;

each of said cover flaps having a first curved portion having a first curvature and being pivotably connected to said base part and a second curved portion extending from said first curved portion;

each of said second curved portions having a free end and a T-shaped thickening at said free end when viewed in a section view lying in a plane perpendicular to said longitudinal axis (A);

said second curved portions having a second curvature greater than said first curvature to guide said T-shaped thickenings inwardly in response to pivoting of said cover flaps to seat on one of said broad sides of said intraocular lens during the movement of said cover flaps toward said closed position whereat said T-shaped thickenings mutually abut to provide a mechanically self-stabilizing structure closed in cross-section;

said inner wall of said support slide being shaped to have a curvature to allow an unimpeded movement of said cover flaps during said movement of said cover flaps in said interior from said base position to said closed position; and, said T-shaped thickenings being seated on said one of said broad sides of said intraocular lens at respective locations thereon spaced away from said peripheral edge thereof.

27. A cassette assembly for insertion into a receptacle of an injector device for introducing an intraocular lens into an eye, the lens having top and bottom broad sides and a peripheral edge extending between said broad sides, the cassette assembly comprising:

a support slide formed as an annular component having an inner wall delimiting an interior;

a cassette accommodating the intraocular lens and defining a longitudinal axis (A);

said inner wall including a roof portion disposed above said cassette;

said cassette being disposed in said interior and including:

a base part;

pivotable cover flaps arranged on said base part so as to be pivotable about said longitudinal axis (A) from a base position to a closed position;

said cover flaps being curved at least in selected regions thereof and being configured to be bendable within said interior so as to deform in a defined manner when said cover flaps are moved from said base position to said closed position;

each of said cover flaps including a first and a second portion extending directly from said first portion, and said first and said second portion having a concave curvature facing toward said longitudinal axis (A) and having first and second radii of curvature, respectively;

said second radius of curvature of said second portion being smaller than said first radius of curvature of said first portion;

said roof portion of said inner wall being shaped to have a radius of curvature to allow an unimpeded movement of said cover flaps during said movement of said cover flaps from said base position to said closed position while within said interior.

28. A cassette assembly for insertion into a receptacle of an injector device for introducing an intraocular lens into an eye, the lens having top and bottom broad sides and a peripheral edge extending between said broad sides, the cassette assembly comprising:

a support slide formed as an annular component having an inner wall delimiting an interior;

a cassette accommodating the intraocular lens and defining a longitudinal axis (A);

said cassette being disposed in said interior and including:

a base part;

pivotable cover flaps arranged on said base part so as to be pivotable about said longitudinal axis (A) from a base position to a closed position;

said cover flaps being curved at least in selected regions thereof and being configured to be bendable within said interior so as to deform in a defined manner when said cover flaps are moved from said base position to said closed position; and, said inner wall being shaped to have a curvature to allow an unimpeded movement of said cover flaps during said movement of said cover flaps from said base position to said closed position within said interior;

wherein said injector device includes closure tips and wherein said cassette assembly further comprises said cover flaps having respective outer sides whereat respective risers are disposed and configured for a guiding contact engagement of said closure tips to apply respective lateral forces to said risers for automatically closing said cover flaps in response to an axial relative displacement between said closure tips and said cassette.

* * * * *